(12) United States Patent
Carson et al.

(10) Patent No.: US 6,951,845 B2
(45) Date of Patent: Oct. 4, 2005

(54) METHOD FOR TREATING ALLERGIC LUNG DISEASE

(75) Inventors: Dennis A. Carson, Del Mar, CA (US); Eyal Raz, Del Mar, CA (US)

(73) Assignee: The Regents of the University of California, Oakland, CA (US)

( * ) Notice: Subject to any disclaimer, the term of this patent is extended or adjusted under 35 U.S.C. 154(b) by 219 days.

(21) Appl. No.: 10/146,717

(22) Filed: May 13, 2002

(65) Prior Publication Data

US 2003/0027782 A1 Feb. 6, 2003

Related U.S. Application Data

(63) Continuation of application No. 09/689,445, filed on Oct. 12, 2000, now Pat. No. 6,426,336, which is a continuation of application No. 09/212,064, filed on Dec. 15, 1998, now Pat. No. 6,174,872, which is a continuation of application No. 08/725,968, filed on Oct. 4, 1996, now Pat. No. 5,849,719, which is a continuation-in-part of application No. 08/333,068, filed on Nov. 1, 1994, now Pat. No. 5,804,566, which is a continuation-in-part of application No. 08/112,440, filed on Aug. 26, 1993, now abandoned.

(51) Int. Cl.[7] ............................ C07H 21/02; C07H 21/04; C12P 21/06; C12N 15/63; A61K 31/70
(52) U.S. Cl. ............................ 514/44; 514/958; 536/23.1; 536/23.5; 536/23.6; 536/23.7; 536/25.3; 435/69.1; 435/440; 435/455
(58) Field of Search ................. 514/44, 958; 536/23.1, 536/23.5, 23.6, 23.7, 25.3; 435/69.1, 440, 455

(56) References Cited

U.S. PATENT DOCUMENTS

| | | | |
|---|---|---|---|
| 5,580,859 A | | 12/1996 | Felgner et al. |
| 5,589,466 A | | 12/1996 | Felgner et al. |
| 5,663,153 A | * | 9/1997 | Hutcherson et al. ........... 514/44 |
| 5,679,647 A | * | 10/1997 | Carson et al. ................. 514/44 |
| 5,723,335 A | * | 3/1998 | Hutcherson et al. ......... 435/375 |
| 5,804,566 A | * | 9/1998 | Carson et al. ................. 514/44 |
| 5,849,719 A | * | 12/1998 | Carson et al. ................. 514/44 |
| 5,985,847 A | * | 11/1999 | Carson et al. ................. 514/44 |
| 6,174,872 B1 | * | 1/2001 | Carson et al. ................. 514/44 |
| 6,194,388 B1 | | 2/2001 | Krieg et al. |
| 6,207,646 B1 | * | 3/2001 | Krieg et al. ................... 514/44 |
| 6,214,806 B1 | * | 4/2001 | Krieg et al. ................... 514/44 |
| 6,218,371 B1 | * | 4/2001 | Krieg et al. ................... 514/44 |
| 6,239,116 B1 | | 5/2001 | Krieg et al. |
| 6,339,068 B1 | * | 1/2002 | Krieg et al. ................... 514/44 |
| 6,406,705 B1 | * | 6/2002 | Davis et al. ............. 424/278.1 |
| 6,426,336 B1 | * | 7/2002 | Carson et al. ................. 514/44 |
| 6,429,199 B1 | * | 8/2002 | Krieg et al. ................... 514/44 |
| 6,451,320 B1 | * | 9/2002 | Stephenne et al. ........ 424/202.1 |
| 6,498,148 B1 | * | 12/2002 | Raz ............................. 514/44 |
| 6,514,948 B1 | * | 2/2003 | Raz et al. ..................... 514/44 |
| 6,534,062 B2 | * | 3/2003 | Raz et al. ................. 424/193.1 |
| 6,544,518 B1 | * | 4/2003 | Friede et al. ............ 424/184.1 |
| 6,552,006 B2 | * | 4/2003 | Raz et al. ..................... 514/44 |
| 6,562,798 B1 | * | 5/2003 | Schwartz ..................... 514/44 |
| 6,610,661 B1 | * | 8/2003 | Carson et al. ................. 514/44 |
| 2001/0044416 A1 | * | 11/2001 | McCluskie et al. ........... 514/44 |
| 2003/0026782 A1 | * | 2/2003 | Krieg ........................ 424/93.2 |
| 2003/0050261 A1 | * | 3/2003 | Krieg et al. ................... 514/44 |
| 2003/0078223 A1 | * | 4/2003 | Raz et al. ..................... 514/44 |
| 2003/0091599 A1 | * | 5/2003 | Davis et al. ............. 424/278.1 |
| 2003/0100527 A1 | * | 5/2003 | Krieg et al. ................... 514/44 |
| 2003/0133988 A1 | * | 7/2003 | Fearon et al. ............... 424/493 |
| 2003/0181406 A1 | * | 9/2003 | Schetter et al. ............... 514/44 |

FOREIGN PATENT DOCUMENTS

| WO | WO 90/11092 | 10/1990 |
|---|---|---|
| WO | WO 98/52962 | 11/1998 |

OTHER PUBLICATIONS

Kandimalla et al, Current Opinion in Molecular Therapeutics, 2002, 4/2:122–129.*
Kreig et al, Antisense and Nucleic Acid Drug Development, 1996, 6:133–139.*
Uhlmann et al, Current Opinion in Drug Discovery and Development, 2003, 6/2:204–217.*
Serebrisky et al, J. Immunology, 2000, 165:5906–5912.*
Aderem et al, Cell, Dec. 2000, 103:993–996.*
Kandimalla et al, Nucleic Acids Research, 2003, 31/9:2393–2400.*
McCkuskie et al, Vaccine, 2001, 19:950–957.*
Klinman et al, Vaccine, 1999, 17:19–25.*
Mackay et al, New England J. Medicine, Jan. 11, 2001, 344/2:109–113.*
Kreig et al, Nature, Apr. 6, 1995, 374:546–549.*
Kreig et al, Trends in Microbiology, Jan. 1998, 6/1:23–27.*
Klinman, Antisense and Nucleic Acid Drug Development, 1998, 8:181–184.*
Roman et al, Nature Medicine, Aug. 1997, 3/8:849–854.*
Horner et al, J. Allergy Clin. Immunol., 2002, 110:431–420.*
Horner et al, J. Allergy Clin. Immunol., 2002, 110:706–712.*
Peng et al, International Immunology, 2001, 13/1:3–11.*
Broide et al, Springer Semin. Immunopathol., 2000, 22:117–124.*

(Continued)

*Primary Examiner*—Nita Minnifield
(74) *Attorney, Agent, or Firm*—Carol L. Francis; Paula A. Borden; Bozicevic, Field & Francis, LLP

(57) ABSTRACT

The invention is directed to a method for treating both the early and late phases of allergic asthma by introducing naked polynucleotides which operatively encode for the asthma-initiating antigen into the host. The antigen-encoding polynucleotides are administered to host tissues which contain a high concentration of antigen presenting cells (e.g., skin and mucosa) relative to other host tissues. Expression of the asthma-initiating antigen encoding polynucleotides of the invention inside of antigen presenting cells (without substantial secretion therefrom) induces antigen tolerance while suppressing IgE antibody formation in the early phase of the disease, and also suppresses cytokine-mediated eosinophil accumulation in the late phase of the disease. Devices and compositions for use in the methods of the invention are also described.

6 Claims, 14 Drawing Sheets

OTHER PUBLICATIONS

Van Uden et al, J. Allergy Clin. Immunol., 1999, 104:902–910.*
Heeg et al, Int. Arch. Allergy Immunol., 2000, 121:87–97.*
Magone et al, Eur. J. Immunol., 2000, 30:1841–1850.*
Kline et al, Am. J. Physiol. Lung Cell Mol. Physiol., 2002, 283:L170–L179.*
Tournaoy et al, Clin. Exp. All., 2002, 31:17–29.*
Marshall et al, J. Allergy, Clin. Immunol., 2001, 108:191–197.*
Broide et al, Int. Arch. Allergy Immunol., 1999, 118:453–456.*
Hartmann et al, PNAS, USA, Aug. 1999, 96:9305–9310.*
Kohama et al, J. Allergy Clin. Immunol., 1999, 104/6:1231–1238.*
Broide et al, J. Immunology, 1998, 161:7054–7062.*
Leonard et al, Biodrugs, 2003, 17/1:1–7.*
Tighe et al, J. Allergy Clin. Immunol., 2000, 106:124–134.*
Broide et al, In: Immunostimulatory DNA Sequences, Editor, Raz, 2001, pp. 117–124.*
Klinman et al, Drug News Perspect, Jun. 2000, 13/5:289–297.*
Yamamoto et al, In: Immunostimulatory DNA Sequences, Editor, Raz, 2001, pp. 11–19.*
Kitagaki et al, In: Microbial DNA and Host Immunity, Editor, Raz, 2002, pp. 301–314.*
Ikeda et al, In: Microbial DNA and Host Immunity, Editor, Raz, 2002, pp. 289–299.*
Horner et al, In: Microbial DNA and Host Immunity, Editor, Raz, 2002, pp. 279–287.*
Spiegelberg et al, Current Opinion in Molecular Therapeutics, 2002, 4/1:64–71.*
Acsadi, et al. "Human dystrophin expression in mdx mice after intramusclular injection of DNA constructs", *Nature,* (1991) vol. 352: 815–818.
Ballas, et al. "Induction of NK activity in murine and human cells by CpG motifs in oligodeoxynucleotides and bacterial DNA", *Journal of Immunology,* (1996) vol. 157: 1840–1845.
Barr, et al. "Systemic delivery of recombinant proteins by genetically modified myoblasts", *Science,* (1991) vol. 254: 1507–1512.
Been, et al. "One binding site determines sequence specificity of tetrahymena Pre–rRNA self splicing, trans–splicing, and RNA enzyme activity", *Cell,* (1986) vol. 47: 207–216.
Caligiuri, et al. "Selective modulation of human natural killer cells in vivo after prolonged infusion of low dose recombinant interleukin 2", *J. Clin. Invest.,* (1993) vol. 91: 123–132.
Chang, et al. "Nasal drug delivery", *Treatise on Controlled Drug Delivery,* pp. 423–463.
Chien. "Mucosal drug delivery: Potential routes for noninvasive systemic administration", *Novel Drug Delivery Systems,* vol. 50: 197–227.
Chien. "Transdermal drug delivery and delivery systems", *Novel Drug Delivery Systems,* vol. 50: 301–380.
Chien. "Nasal drug delivery and delivery systems", *Novel Drug Delivery Systems,* vol. 50: 229–268.
Chua, et al. "Sequence analysis of cDNA coding for a major house dust mite allergen", *J. Exp. Med.,* (1988) vol. 167: 175–182.
Davis, et al. "Plasmed DNA Is superior to viral vectors for direct gene transfer into adult mouse skeletal muscle", *Human Gene Therapy,* (1993) vol. 4: 733–740.
Del Rey, et al. "Antidiabetic effects of interleukin 1", *Proc. Natl. Acad. Sci. USA,* (1989) vol. 86: 5943–5947.
Donohue, et al. "In vivo administration of purified jurkat-derived interleukin 2 in mice", *Cancer Research,* (1984) vol. 44: 1380–1386.
Goldstein, et al. "Repetitive weekly cycles of interleukin 2: Effect of outpatient treatment with a lower dose of interleukin 2 . . . ", *Cancer Research,* (1989) vol. 49: 6832–6839.
Gorman, et al. "The rous sarcoma virus long terminal repeat is a strong promoter when introduced into a variety of eukaryotic cells . . . ", *Proc. Natl. Acad. Sci. USA,* (1982) vol. 79: 6777–6781.
Hefeneider, et al. "In vivo interleukin 2 administration augments the generation of alloreactive cytolytic T lymphocytes and resident natural killer cells", *Journal of Immunology,* (1983) vol. 130(1): 222–227.
Hoyne, et al. *Immunology and Cell Biology,* (1986) vol. 74: 180–188.
Kaplan, et al. "Rational immunotheraphy with interleukin 2", *Bio/Technology,* (1992) vol. 10: 157–162.
Kemeny, et al. "CD8+ T cells in allergy", *Allergy,* (1992) vol. 47: 12–21.
Krieg, et al. "Functional messenger RNAs are produced by SP6 in vitro transcription of cloned cDNAs", *Nucleic Acids Research, IRL Press Limited,* (1984) vol. 12(18): 7057–7070.
Krieg, et al. "CpG motifs in bacterial DNA trigger direct B–cell activation", *Nature,* (1995) vol. 374: 546–549.
Krieg, et al. "Oligodeoxynucleotide modifications determine the magnitude of B cell stimulation by CpG motifs", *Antisense and Nucleic Acid Drug Development,* (1996) vol. 6: 133–139.
Kuramoto, et al. "Oligonucleotide sequences required for natural killer cell activation", *Jpn. J. Cancer Res.,* (1992) vol. 83: 1128–1131.
Lotz, et al. "β cell stimulating factor 2/Interleukin 6 is a costimulant for human . . . ", *J. Exp. Med.,* (1988) vol. 167: 1253–1258.
Mader, et al. *PNAS,* (1993) vol. 90: 5603.
Multi–Test, Lincoln Diagnostics, Inc., pp. 1–6.
Norton, et al. "Bacterial B–galactosidase as a marker of rous sarcoma virus gene expression and replication", *Molecular and Cellular Biology,* (1985) vol. 5(2): 281–290.
Robinson, et al. "Use of direct DNA inoculations to elicit protective immune responses", *Journal of Cellular Biochemistry,* (1993) Supp. vol. 17D: 92.
Secrist, et al. "Allergen immunotherapy decreases interleukin 4 production in CD4+ T cells from allergic individuals", *J. Exp. Med.,* (1993) vol. 178: 2123–2130.
Shields, et al. "Calorie restriction suppresses subgenomic mink cytopathic focus–forming murine leukemia virus transcription and frequency . . . ", *Proc. Natl. Acad. Sci. USA,* (1991) vol. 88: 11138–11142.
Sloan. "Use of solubility parameters from regular solution theory to describe partitioning–driven processes". *Prodrugs: Topical and Ocular Drug Delivery,* vol. 53: 179–204.
Stribling, et al. "Aerosol gene delivery in vivo", *Proc. Natl. Acad. Sci. USA,* (1992) vol. 89 : 11277–11281.

Tang, et al. "Genetic immunization is a simple method for eliciting an immune response", *Nature,* (1992) vol. 356: 152–154.

Teppler, et al. "Prolonged immunostimulatory effect of low–dose polyethylene glycol interleukin 2 in patients with human immunodeficiency virus type 1 infection", *J. Exp. Med.,* (1993) vol. 177: 483–492.

Terr. "Allergy desensitization", pp. 739–743.

Tice, et al. "Parenteral drug delivery: Injectables", *Treatise on Controlled Drug Delivery,* pp. 315–339.

Ulmer, et al. "Heterologous protection against influenza by injection of DNA encoding a viral protein", *Science,* (1993) vol. 259: 1745–1748.

Wolff, et al. "Conditions affecting direct gene transfer into rodent muscle in vivo", *BioTechniques,* (1991) vol. 11(4): 474–485.

* cited by examiner

METHOD FOR TREATING ALLERGIC LUNG DISEASE

RELATED PATENT APPLICATIONS

This application is a continuation of U.S. patent application Ser. No. 09/689,445, filed Oct. 12, 2000, now U.S. Pat. No. 6,426,336, which is a continuation of U.S. patent application Ser. No. 09/212,064, filed Dec. 15, 1998, now U.S. Pat. No. 6,174,872, which is a continuation of U.S. patent application Ser. No. 08/725,968, filed Oct. 4, 1996, now U.S. Pat. No. 5,849,719, which is a continuation-in-part of U.S. patent application Ser. No. 08/333,068, filed Nov. 1, 1994, now U.S. Pat. No. 5,804,566, which is in turn a continuation-in-part of U.S. patent application Ser. No. 08/112,440, filed Aug. 26, 1993, now abandoned.

STATEMENT OF GOVERNMENT RIGHTS

This invention may have been made with Government support under Grant Nos. AR07567 and AR25443, awarded by the National Institutes of Health. The Government may have certain rights in this invention.

BACKGROUND OF THE INVENTION

1. Field of the Invention

The invention relates to a method for treating both the early and late phases of allergic lung disease. In particular, the invention relates to a method for immunizing a host against allergic asthma through use of asthma-initiating antigen-encoding polynucleotide compositions.

2. History of the Prior Art

Asthma is one of the common chronic lung diseases of industrialized countries. The airway narrowing which characterizes the disease is associated with antigen stimulated immune system activation, including elevation of antigen-specific IgE levels in the early phase of the disease and eosinophil infiltration of lung tissue in the late phase of the disease.

Specifically, during the early phase of the disease, activation of Th2 lymphocytes stimulates the production of IgE antibody, which in turn triggers the release of histamine and other immune mediators from mast cells. During the late phase of the disease, IL-4 and IL-5 cytokine production by CD4+ helper T lymphocyte type 2 (Th2) cells is elevated. These cytokines are believed to play a significant role in recruiting eosinophils into lung tissue, where tissue damage and dysfunction result.

Persons suffering from allergic asthma are conventionally treated by immunization against the asthma-initiating antigen with an antigen-based composition. Antigen immunization limits the antigen-stimulated events of the early phase of allergic asthma, albeit at the risk of inducing IgE mediated anaphylaxis. However, such classical immunization schemes do not target the cytokine-mediated events of the late phase immune response in allergic asthma.

SUMMARY OF THE INVENTION

The invention consists of a method for treating allergic asthma in a host which reduces the allergic immune responses that are characteristic of both the early and late phases of the disease. This is accomplished according to the invention by administering an asthma-initiating antigen-encoding polynucleotide to the host in a manner which induces intracellular expression of the antigen in antigen presenting cells. The expressed antigen is presented to host $CD4^+$ T lymphocytes in a manner which activates class 1 helper T (Th1) lymphocytes in preference to Th2 lymphocytes.

Thus, the polynucleotide immunization scheme of the invention allows the clinician to induce tolerance to an asthma-initiating antigen in a host with little risk of stimulating the Th2 lymphocyte mediated IgE antibody production and mast cell activation events which characterize the early phase of allergic asthma. In addition, the immunization scheme of the invention also reduces Th2 cell release of IL-4 and IL-5, thus substantially limiting the eosinophil accumulation in lung tissue which characterizes the late phase of allergic asthma. In this manner, the invention provides a more efficacious, less risk-intensive means of treating allergic asthma than is presently available in the art.

In practice, a suitable candidate for treatment according to the method of the invention is a host in whom allergic asthma has been diagnosed and for whom at least one asthma-initiating antigen (i.e., a proteinaceous antigen which triggers an allergic response in the host that results in asthmatic symptoms being experienced by the host) has been identified.

According to the method of the invention, the host is immunized with a pharmaceutical composition comprised of a recombinant expression vector (preferably a plasmid or cosmid, hereafter "polynucleotide composition"). The recombinant expression vector incorporates a polynucleotide which encodes the asthma-initiating antigen. To enhance Th1 lymphocyte activation to a therapeutically sufficient level, the polynucleotide composition is administered to a tissue of the host which contains a relatively high concentration of antigen presenting cells (e.g., skin or mucosa, such as the mucosa of the respiratory tract) as compared to other host tissues. Advantageously, targeting the dense population of antigen presenting cells present in the skin and mucosa for expression of antigen permits relatively minute doses of polynucleotide composition to be applied toward a therapeutic effect in the host.

Where desired, the recombinant expression vector of the polynucleotide composition may also code for other therapeutically significant, biologically active peptides, such as immunostimulatory cytokines (e.g., TGF-β). Alternatively, such peptides or other therapeutically significant compounds may be administered in conjunction with the polynucleotide compositions of the invention.

DETAILED DESCRIPTION OF THE INVENTION

Figure 1:
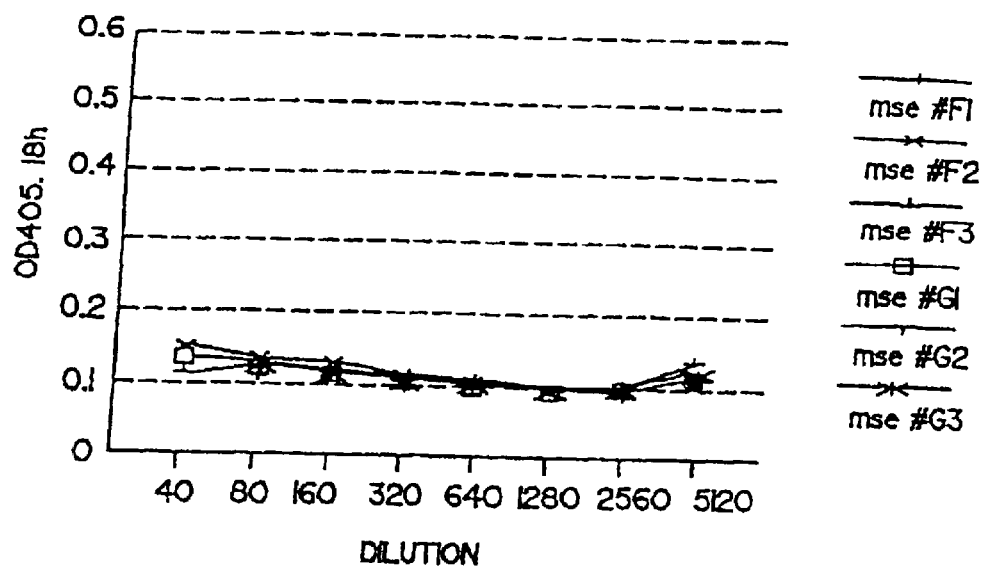
FIG. 1 depicts the results of an ELISA for anti-NP IgG before intranasal introduction of naked pCMVRNP to Balb/c mice.

Throughout this description, the preferred embodiment and examples shown should be considered as exemplars, rather than limitations on the invention.

I. Definitions

The following definitions are provided to simplify discussion of the invention. Those skilled in the art will, however, recognize that these definitions may be expanded to include equivalents without departing from the legitimate scope or spirit of the invention. For this reason, these definitions should not be construed as limiting the invention.

a. "Polynucleotide" refers to DNA or RNA and can include sense and antisense strands as appropriate to the goals of the therapy practiced according to the invention. Polynucleotide in this context may include oligonucleotides. Polynucleotides useful in the invention are those which are incorporated into recombinant expression vectors that include promoter and other sequences necessary for expression of the desired translation product(s); e.g., a peptide or protein. The method of the invention can be practiced using known either viral or non-viral recombinant expression vectors, although the latter are preferred. Preferably, these vectors will incorporate complementary DNA (cDNA) which encode for the desired translation product(s).

b. "Polynucleotide composition" refers to a pharmaceutically safe polynucleotide free of a delivery vehicle (such as liposomes or colloidal particles); i.e., a "naked" polynucleotide in a carrier which will not impair antigen recognition of the polynucleotide.

c. "Asthma-initiating Antigen" refers to one or more proteinaceous antigens (1) to which the host has been determined to be allergic; and (2) which stimulate asthmatic symptoms in the host.

d. "Antigen Presenting Cells" or "APC's" include known APC's such as Langerhans cells, veiled cells of afferent lymphatics, dendritic cells and interdigitating cells of lymphoid organs. The definition also includes mononuclear cells such as (1) lymphocytes and macrophages which take up and express polynucleotides according to the invention in skin and (2) mononuclear cells (e.g., as depicted in histological photographs contained herein). These cells are not tissue cells but are likely to be antigen presenting cells. The most important of these with respect to the present invention are those APC's which are known to be present in high numbers in epithelia and thymus dependent areas of the lymphoid tissues, including epidermis and the squamous mucosal epithelia of the buccal mucosa, vagina, cervix and esophagus (areas with "relatively high" concentrations of APC's). In addition to their definitions set forth below, therefore, "skin" and "mucosa" as used herein particularly refer to these sites of concentration of APC's.

e. "Host" refers to the recipient of the therapy to be practiced according to the invention. The host may be any vertebrate, but will preferably be a mammal. If a mammal, the host will preferably be a human, but may also be a domestic livestock, laboratory subject or pet animal.

f. "Target tissue" refers to the tissue of the host in which expression of a polynucleotide is sought.

g. "Skin" as used herein refers to the epidermal, dermal and subcutaneous tissues of a host.

h. "Mucosa" refers to mucosal tissues of a host wherever they may be located in the body including, but not limited to, respiratory passages (including bronchial passages, lung epithelia and nasal epithelia), genital passages (including vaginal, penile and anal mucosa), urinary passages (e.g., urethra, bladder), the mouth, eyes and vocal cords. Respiratory passages are the primary target tissue for introduction of polynucleotide compositions to treat allergic asthma according to the invention.

i. "Point of Entry" refers to the site of introduction of the naked polynucleotide into a host, including immediately adjacent tissue.

j. "Th1/Th2 Response(s)" refer, respectively, to types 1 and 2 helper T lymphocyte (Th) mediated immune responses. Th2 responses include the allergy-associated IgE antibody class as well as elevated levels of IL-4 and IL-5 cytokines by Th2 lymphocytes. Soluble protein antigens tend to stimulate relatively strong Th2 responses. In contrast, Th1 responses are induced by antigen binding to macrophages and dendritic cells. that is induced preferentially by antigens that bind to and activate certain APC's; i.e., macrophages and dendritic cells. Th1 cells secrete IL-2, interferon (IFN)-γ and tumor necrosis factor (TFN)-β (the latter two of which are involved in macrophage activation and delayed-type hypersensitivity in response to antigen stimulation).

k. "Synthesis" refers to well-known means of synthesizing polynucleotide sequences and may include isolation and purification of native polynucleotides.

l. "Peptide" refers to small peptides, polypeptides, oligopeptides and proteins which have a desired biological effect in vivo.

m. "Iontophoresis" refers to a known means of transdermal transmission presently used to deliver peptides continuously to a host. More specifically, it is a process that facilitates the transport of ionic species by the application of a physiologically acceptable electrical current. This process and other transdermal transmission means are described in Chien, et al. *Transdermal Drug Delivery*, "Novel Drug Delivery Systems", Ch. 7, part C, (Marcel Dekker, 1992), the relevant disclosures of which are incorporated herein by this reference for the purpose of illustrating the state of knowledge in the art concerning techniques for drug delivery.

n. "Detergents/Absorption Promoters" refers to chemical agents which are presently known in the art to facilitate absorption and transfection of certain small molecules, as well as peptides.

o. "Dermal" and "Epidermal Administration" mean routes of administration which apply the naked polynucleotide(s) to or through skin. Dermal routes include intradermal and subcutaneous injections as well as transdermal transmission. Epidermal routes include any means of irritating the outermost layers of skin sufficiently to provoke an immune response to the irritant. The irritant may be a mechanical or chemical (preferably topical) agent.

p. "Epithelial Administration" involves essentially the same method as chemical epidermal administration, except that the chemical irritant is applied to mucosal epithelium.

q. "IL" refers to interleukin.

r. "IFN" refers to interferon.

II. Discussion

A. Theory of the Invention

The method of the invention exploits the unexpected discovery that asthma-initiating antigen-encoding polynucleotide compositions which are taken up and expressed in host APCs (1) stimulate production of Th1 lymphocytes in preference to Th2 lymphocytes; (2) consequently suppress the IgE antibody production characteristic of the early phase of allergic asthma; and (3) consequently reduce the IL-4/IL-5 stimulated eosinophil infiltration of lung tissue characteristic of the late phase of the disease. Notably, administration of polynucleotide compositions which encode asthma-initiating antigens (or fragments thereof) not only suppresses IgE antibody production, but also does so from the outset of therapy, thus reducing the risk of anaphylaxis posed by classical immunotherapy. Thus, the method of the invention effectively and immediately manipulates the T lymphocyte compartment of the host immune response to reduce both the IgE and cellular immune-mediated events associated with allergic asthma.

More specifically, the method of the invention introduces asthma-initiating antigens into the intracellular compartment of host APCs present in the target tissue, where the antigen is retained without substantial secretion therefrom (see, Examples IV through VII). This intracellular expression and retention of antigen preferentially stimulates Th1 responses against the antigen. Because the Th2 response to extracellular antigen achieved in classical immunotherapy is avoided, IgE production and IL-4/IL-5 release in response to extracellular antigen is also avoided.

For example, as shown in Examples VII and VIII, IgE and IL-4 levels in expressed antigen-challenged mice were surprisingly very low, while asthma-initiating antigen-specific CTL levels (Example IX) and Th1 cell secretion of INFγ (Example VIII) were enhanced (as compared to protein challenged and control mice). The suppression of IgE and IL-4 production achieved in mice immunized according to the invention continued despite subsequent challenge with the plasmid or protein, even when combined with adjuvant (Examples VII–VIII). Thus, while both mice challenged with protein antigen and mice immunized according to the invention developed IgG mediated tolerance to the immunizing antigen, the latter mice suffered far less from the IgE mediated immune events which characterize the early phase of allergic asthma.

In addition, mice immunized according to the invention fare better in the late phase of allergic asthma than do protein-antigen immunized mice. In particular, the data in Example II demonstrate that administration of ovalbumin antigen-encoding polynucleotide compositions to murine models for allergic asthma produced (with adjuvant) up to a 90% reduction in eosinophil infiltration of lung tissue in the mice on subsequent asthma-initiating antigen challenge, as compared to control mice. Thus, the mice immunized according to the invention were protected from eosinophil infiltration of lung tissue far better than their protein-antigen immunized litter mates.

Thus, in contrast to classical allergic asthma immunotherapy, the asthma-initiating antigen-encoding gene immunotherapy of the invention abrogates both asthma-initiating antigen-specific and non-specific IgE production in the early phase of allergic asthma, protects the host from further production of IgE even on subsequent asthma-initiating antigen challenge, and reduces cellular lung infiltration and airway hypersensitivity in the late phase of the disease.

B. Polynucleotide Compositions Useful in the Invention

1. Useful Antigen-Encoding Polynucleotides and Recombinant Expression Vector Constructs In allergic asthma, the symptoms of the disease are triggered by an allergic response in a host to an allergen. The polynucleotide sequences of many nucleic acids which code for asthma-initiating antigen allergens are known. All such polynucleotide sequences are useful in the method of the invention. Examples of some of the more common allergens for use in the invention are set forth below; those of ordinary skill in the art will be familiar with additional examples, the use of which is encompassed by the invention.

For use in the method of the invention, the recombinant expression vector component of the polynucleotide compositions of the invention may encode more than one asthma-initiating antigen, different peptides of an asthma-initiating antigen, or a combination of the two. The polynucleotides may encode for intact asthma-initiating antigen or T cell epitope(s) of an asthma-initiating antigen, engineered by means well-known in the art to be non-secreting.

As noted above, many asthma-initiating antigen-encoding polynucleotides are known in the art; others can be identified using conventional techniques such as those described elsewhere below. Examples of known asthma-initiating antigen-encoding polynucleotides include cDNAs which code for IgE reactive major dust mite asthma-initiating antigens Der pI and Der pII (see, Chua, et al., *J. Exp. Med.,* 167:175–182, 1988; and, Chua, et al., *Int. Arch. Allergy Appl. Immunol.,* 91:124–129, 1990), T cell epitope peptides of the Der pII asthma-initiating antigen (see, Joost van Neerven, et al., *J. Immunol.,* 151:2326–2335, 1993), the highly abundant Antigen E (Amb aI) ragweed pollen asthma-initiating antigen (see, Rafnar, et al., *J. Biol. Chem.,* 266:1229–1230, 1991), phospholipase $A_2$ (bee venom) asthma-initiating antigen and T cell epitopes therein (see, Dhillon, et al., *J. Allergy Clin. Immunol.,* 90:42–51, 1992), white birch pollen (Betvl) (see, Breiteneder, et al., *EMBO,* 8:1935–1938, 1989), and the Fel dI major domestic cat asthma-initiating antigen (see, Rogers, et al., *Mol. Immunol.,* 30:559–568, 1993). The published sequences and methods for their isolation and synthesis described in these articles are incorporated herein by this reference to illustrate knowledge in the art regarding asthma-initiating antigen-encoding polynucleotides.

In addition, expression (by the same or a different recombinant expression vector) or co-administration of therapeutically beneficial peptides such as TGF-β, TNF-β, IL-2 and IFN-γ enhance the Th1 response sought by the method of the invention. IL-2 and IFN-γ are of particular interest in this regard because, in recent clinical trials, IL-2 and gamma interferon have proved toxic at dosages sufficient to interfere with production of IgE.

The polynucleotides to be used in the invention may be DNA or RNA, but will preferably be a complementary DNA (cDNA) sequence. The polynucleotide sequences used in the invention must be (a) expressible and (b) either non-replicating or engineered by means well known in the art so as not to replicate into the host genome. Illustrations of the preparation of polynucleotides suitable for use in the invention follow. It will, however, be apparent to those skilled in the art that other known means of preparing nonreplicating polynucleotides may also be suitable.

In general, DNA sequences for use in producing therapeutic and/or immunogenic peptides of the invention can be obtained by several methods. For example, the DNA can be isolated using hybridization procedures which are well known in the art. These include, but are not limited to: 1) hybridization of probes to genomic or cDNA libraries to detect shared nucleotide sequences; 2) antibody screening of expression libraries to detect shared structural features and 3) synthesis by the polymerase chain reaction (PCR). The development of specific DNA sequences encoding or fragments thereof, can also be obtained by: 1) isolation of double-stranded DNA sequences from the genomic DNA: 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded (cDNA) complement of mRNA.

A cDNA library believed to contain a polynucleotide of interest can be screened by injecting various mRNA derived from cDNAs into oocytes, allowing sufficient time for expression of the cDNA gene products to occur, and testing for the presence of the desired cDNA expression product, for example, by using antibody specific for a peptide encoded by the polynucleotide of interest or by using probes for the repeat motifs and a tissue expression pattern characteristic of a peptide encoded by the polynucleotide of interest. Alternatively, a cDNA library can be screened indirectly for expression of therapeutic and/or immunogenic peptides having at least one epitope using antibodies specific for the peptides. Such antibodies can be either polyclonally or monoclonally derived and used to detect expression product indicative of the presence of cDNA of interest.

Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA.

The polynucleotide which encodes each asthma-initiating antigen may be conjugated to or used in association with other polynucleotides which code for regulatory proteins that control the expression of these polypeptides or may contain recognition, promoter and secretion sequences. Those of ordinary skill in the art will be able to select regulatory polynucleotides and incorporate them into the polynucleotide compositions of the invention (if not already present therein) without undue experimentation. For example, suitable promoters for use in murine or human systems and their use are described in *Current Protocols in Molecular Biology,* supra at Ch. 1.

Together with appropriate regulatory sequences, polynucleotide(s) for use in the invention are incorporated into a recombinant expression vector, preferably a non-viral plasmid or cosmid vector. Use of a non-viral vector, particularly one which comprises a replicator, will prolong expression of the gene in target tissues. Certain plasmid vectors are also good mediators of immune responses to immunogenic peptides because high levels of expression are achieved when the gene encoding the peptides is incorporated into the vector.

The recombinant expression vectors (both viral and non-viral) most preferred for use in the invention are described in detail in co-pending, commonly assigned U.S. patent application Ser. No. 08/593,554, the disclosure of which is incorporated herein by reference for the purpose of illustrating vectors useful in the invention. Briefly, the preferred expression vectors for use in the invention include at least one palindromic, non-coding region (i.e., a region where the nucleotide sequence of one strand is the reverse complement of a corresponding region of the complementary strand) of at least 6 nucleotides in length. Each such palindromic region includes an unmethylated CG dinucleotide sequence; i.e., at least two adjacent nucleotides, where one such nucleotide is a cytosine and the other such nucleotide is a guanine.

In double-stranded molecules, each CG dinucleotide sequence present in the palindromic region is itself palindromic; i.e., the cytosine of the CG sequence on one strand is paired with a guanine in a CG sequence on the complementary strand. In single-stranded molecules, the relative position of each CG sequence in the palindromic dinucleotide is preferably 5'-CG'3'. Most-preferably, each CG dinucleotide sequence present in the palindromic region of the preferred expression vectors is flanked by at least two purine nucleotides (e.g., GA or AA) and at least two pyrimidine nucleotides (e.g., TC or TT). Examples of specific expression vector constructs useful in immunizing a host are set forth in co-pending, commonly assigned application Ser. No. 08/593,554.

Such expression vector constructs possess the advantage of stimulating cytotoxic T lymphocyte (CTL) activity to a greater degree than occurs on introduction into a host of control vectors which lack the palindromic sequences described above. In addition, those expression vectors which incorporate the flanking purine and pyrimidine nucleotides as described above also enhance stimulation of B lymphocyte activity in response to expressed initiating antigen. Thus, the expression vectors described above are preferred for their activity as immunostimulatory adjuvants to boost the host immune response to the initiating antigen which is expressed to immunize the host according to the method of the invention.

Other particularly useful recombinant expression vectors for use in the invention are those which incorporate a promoter that can be switched "on" or "off" after the vector has been administered to the patient. Use of such expression vectors in the invention aids in minimizing, if not avoiding, extracellular stimulation of IgE antibody formation against expressed asthma-initiating antigen.

Particularly efficacious examples of such promoters are the ligand inducible nuclear receptor promoters. Nuclear receptors represent a family of transcriptional enhancer factors that act by binding to specific DNA sequences found in target promoters known as response elements. Specific members of the nuclear receptor family include the primary intracellular targets for small lipid-soluble ligands, such as vitamin $D_3$ and retinoids, as well as steroid and thyroid hormones ("activating ligands").

Figure 11:
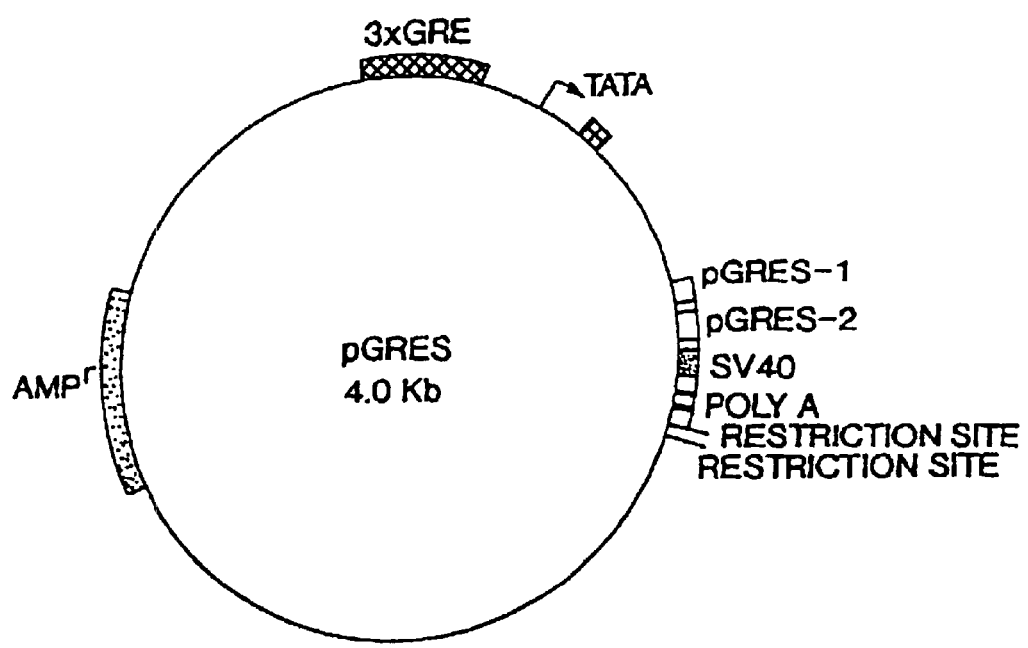
FIG. 11 is a map of the pGREtk eukaryotic expression vector.

Nuclear receptors activated by specific activating ligands are well suited for use as promoters in eukaryotic expression vectors since expression of genes can be regulated simply by controlling the concentration of ligand available to the receptor. For example, glucocorticoid-inducible promoters such as that of the long terminal repeat of the mouse mammary tumor virus (MMTV) have been widely used in this regard because the glucocorticoid response elements are expressed in a wide variety of cell types. One expression system which exploits glucocorticoid response elements responsive to a wide variety of steroid hormones (e.g., dexamethasone and progesterone) is a pGREtk plasmid (containing one or more rat tyrosine amino transferase glucocorticoid response elements upstream of the herpes simplex virus thymidine kinase (tk) promoter in pBLCAT8+), transfected in HeLa cells (see, Mader and White, *Proc. Natl. Acad. Sci USA,* 90:5603–5607, 1993 [pGRE2tk]; and, Klein-Hitpass, et al., *Cell,* 46:1053–1061, 1986 [pBLCAT8+]; the disclosures of which are incorporated herein by this reference to illustrate knowledge in the art concerning construction of suitable promoters derived from nuclear receptor response elements ["NRRE promoters"]). The pGREtk promoter (see, map at FIG. 11) is particularly effective in stimulating controlled overexpression of cloned genes in eukaryotic cells (Mader and White, supra at 5607).

Another particularly suitable NRRE promoter for use in the invention is one which is inducible by the vitamin $D_3$ compound 1,25-dihydroxyvitamin $D_3$ and non-hypercalcemic analogs thereof (collectively, "vitamin $D_3$ activating ligands"). NRRE promoters inducible by vitamin $D_3$ activating ligands contain the vitamin $D_3$ receptor (VDR) response elements PurG(G/T)TCA which recognizes direct repeats separated by 3 base pairs. Vitamin $D_3$ response elements are found upstream of human osteocalcin and mouse osteopontin genes; transcription of these genes is activated on binding of the VDR (see, e.g., Morrison and Eisman, *J. Bone Miner. Res.,* 6:893–899, 1991; and, Ferrara, et al., *J. Biol. Chem.,* 269:2971–2981, 1994, the disclosures of which are incorporated herein by this reference to illustrate knowledge in the art of vitamin $D_3$ responsive inducible promoters). Recent experimental results from testing of a recombinant expression vector containing the mouse osteopontin VDR upstream of a truncated herpes simplex virus thymidine kinase (tk) promoter suggested that 9-cis-retinoic acid can augment the response of VDR to 1,25-hydroxyvitamin $D_3$ (see, Carlberg, et al., *Nature,* 361:657–660,1993).

Figure 12:
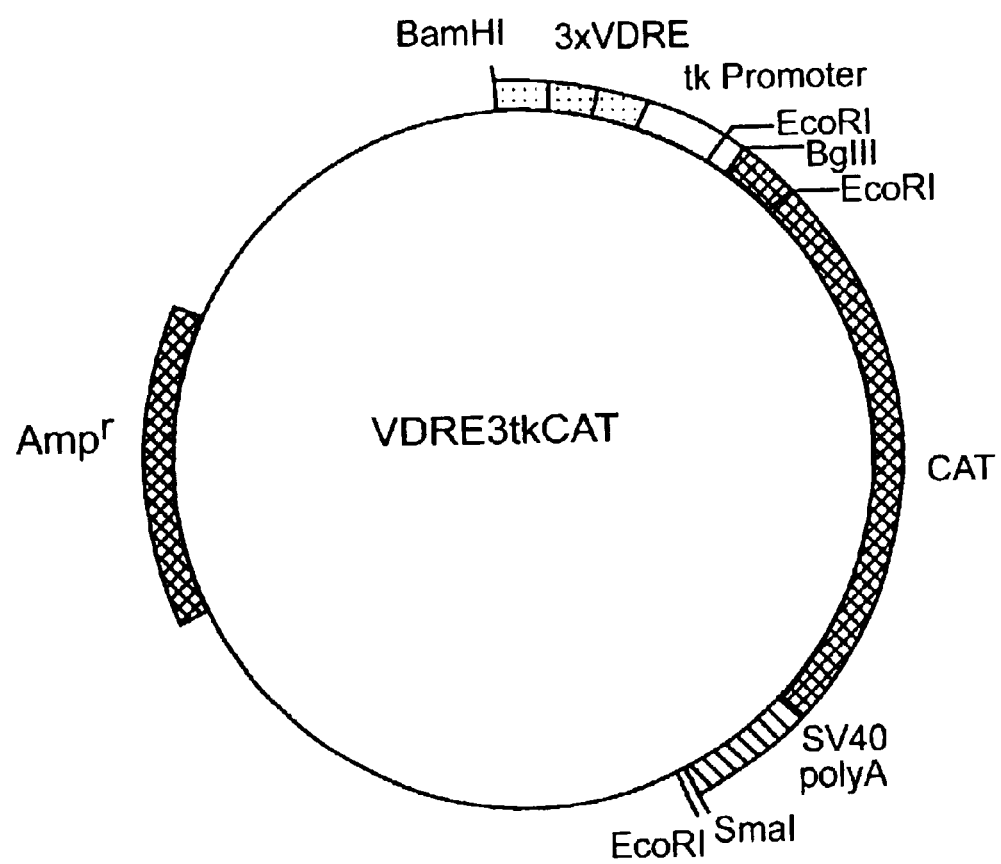
FIG. 12 is a map of the pVDRtk eukaryotic expression vector.

Ferrara, et al. also described vitamin $D_3$ inducible promoters in recombinant expression vectors constructed using multiple copies of a strong VDR; in particular, the mouse osteopontin VDR (composed of a direct repeat of PurGT-TCA motifs separated by 3 base pairs). This VDR conforms to the PurGG/TTCA consensus motifs which have previously been shown to be responsive not only to vitamin $D_3$, but also to thyroid hormone and/or retinoic acid. As many as three copies of the mouse VDR was inserted into pBLCAT8+; immediately upstream of the herpes simplex virus tk promoter (see, e.g., FIG. 12 [map of pVDREtk]). Transfection of the resulting VDREtk vector into COS cells (producing a "VDR expression system") proved to be particularly useful in that COS cells contain the nuclear retinoid X receptor (RXR) that has been shown to act as an auxiliary factor for binding of VDR to its response element.

The VDR expression system (and functionally equivalent expression systems under the control of, for example, human osteocalcin gene promoter) is uniquely suited for use in the invention. Specifically, expression of initiating antigen administered to a mammal according to the invention by epidermal or dermal routes (particularly the former) in a vitamin $D_3$ responsive expression system can be switched on by topical administration of a 1,25-dihydroxyvitamin $D_3$ preparation at the point of entry (and off by withdrawing the vitamin $D_3$ preparation and/or modulated by applying or withdrawing a source of retinoic acid to or from the point of entry). Conveniently, 1,25-dihydroxyvitamin $D_3$ and non-hypercalcemic analogs thereof have been approved for use in topical preparations by the United States Food and Drug Administration for the treatment of psoriasis and are commercially available.

In vivo tests of the NRRE promoters in human skin indicate that they are inducible on systemic exposure to their corresponding response elements (see, Tsou, et al., *Exp. Cell Res.,* 214:27–34, 1994 [retinoic acid activation of retinoic acid response element coupled to a Lac-Z reporter molecule in epidermis of transgenic mice]). Given the expected retention of polynucleotides administered dermally or epidermally at the point of entry (thus making them available for exposure to topically absorbed response elements; see, e.g., discussion at pages 15–16 and data in Example IV), it can be reasonably predicted that use of NRRE promoters for expression of such polynucleotides will also permit their in vivo control through topical administration of appropriate NRRE promoter activating ligands (e.g , 1,25-dihydroxyvitamin $D_3$ transcriptional activators with a VDR expression vector for expression of the polynucleotide of interest).

Thus, use of an NRRE promoter recombinant expression vector for administration and expression of initiating antigens according to the invention permits control of expression to, for example, switch on expression when dosing is needed or switch off expression in the event of an adverse reaction to the expressed protein or peptide.

2. Pharmaceutically Effective Polynucleotide Compositions for Use in the Method of the Invention Compositions of polynucleotide(s) prepared as described above may be placed into a pharmaceutically acceptable carrier for introduction into a host. The carrier chosen should not impair antigen recognition of the polynucleotide composition; for this reason, liposomal and colloidal particle-based delivery vehicles are not desirable for use in the invention. Thus, polynucleotide compositions suitable for use in the invention will most preferably consist of "naked" polynucleotides in a pharmaceutically safe carrier.

Pharmaceutically acceptable carriers may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Further, a may be lyophilized using means well known in the art, for subsequent reconstitution and use according to the invention.

Absorption promoters, detergents, chemical irritants or mechanical irritation means can enhance transmission of the polynucleotide composition through the point of entry. For reference concerning general principles regarding promoters and detergents which have been used with success in mucosal delivery of organic and peptide-based drugs, see Chien, *Novel Drug Delivery Systems*, Ch. 4 (Marcel Dekker, 1992). Specific information concerning known means and principles of nasal drug delivery are discussed in Chien, supra at Ch 5. Examples of suitable nasal absorption promoters are set forth at Ch. 5, Tables 2 and 3; milder agents are preferred. Further, known means and principles of transdermal drug delivery are also discussed in Chien, supra, at Ch. 7. Suitable agents for use in the method of this invention for mucosal/nasal delivery are also described in Chang, et al., *Nasal Drug Delivery*, "Treatise on Controlled Drug Delivery", Ch. 9 and Table 3–4B thereof, (Marcel Dekker, 1992). Suitable agents which are known to enhance absorption of drugs through skin are described in Sloan, *Use of Solubility Parameters from Regular Solution Theory to Describe Partitioning-Driven Processes*, Ch. 5, "Prodrugs: Topical and Ocular Drug Delivery" (Marcel Dekker, 1992), and at places elsewhere in the text.

It is expected that these techniques (and others which are conventionally used to facilitate drug delivery) may be adapted to preparation of polynucleotide compositions for use in the methods of the invention by those of ordinary skill in the art without undue experimentation. In particular, although the approaches discussed in the preceding paragraphs have not, to the inventors' knowledge, been previously used for polynucleotide delivery, it is believed that they are suitable for use to that end. For that reason, the references identified above, while not essential to the inventive methods, are incorporated herein by this reference.

C. Means For, And Routes of, Administration of Polynucleotide Compositions

Although it is not intended that the invention will be entirely limited by a particular theory as to the mechanism of expression involved, it is believed that a biological response in these tissues following administration of the polynucleotide compositions of the invention into skin or mucosa is achieved because the polynucleotide is expressed intracellularly in the cytoplasm of mononuclear cells, most likely the host's antigen presenting cells.

Figure 4:
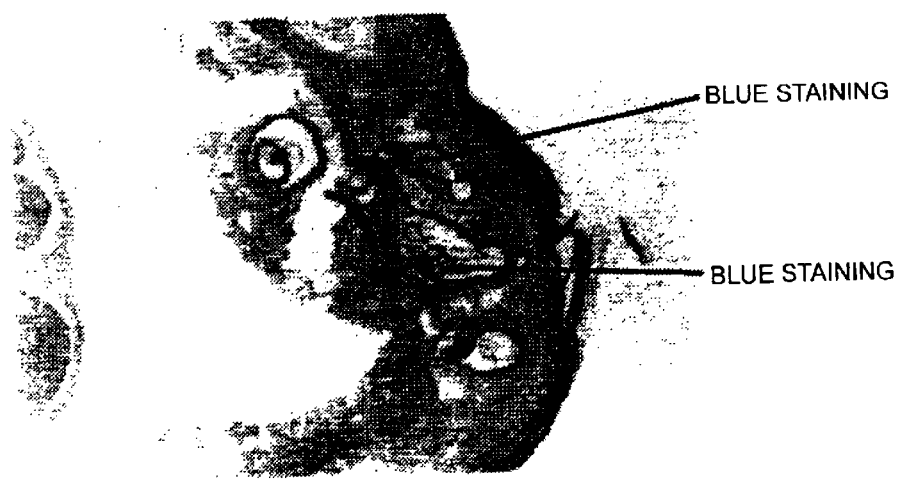
FIG. 4 is a photograph of the results of histological studies of skin at the point of entry for pCMVRNP in Balb/c mice showing uptake of the plasmid by mononuclear cells (APC's). An APC is indicated by an arrows; a tissue cell (not containing the plasmid) is indicated by a slashed line.

More specifically, polynucleotide compositions do not appear to be taken up directly by fibroblasts or other tissue cells in significant quantities (see, histological study in Example IV and FIG. 4). This conclusion is borne out by studies showing that (1) intradermal administration of even minute amounts of polynucleotide compositions into mice induced a prominent Th1 response (indicative of antigen presentation by macrophages and dendritic cells; see, Examples V and VII); (2) intradermal administration of polynucleotide composition to mice induced the formation of cytotoxic T cells without stimulating production of detectable levels of antibody (see, Example VIII); and, (3) induction of prolonged immunological memory with respect to the polynucleotide expression product as an antigen (Example X). It therefore appears that the immunogeneity of polynucleotide compositions depends not on the amount of protein expressed thereby, but instead in part on the type of cell transfected (e.g., antigen presenting cells versus tissue cells).

Therefore, the ideal target tissue will be one in which approximately 1% to 2% of the cell population is comprised of antigen presenting cells; e.g., mucosa or skin. The mucosa of the respiratory tract is the primary target tissue for immunization against asthma-initiating antigens to treat allergic asthma; however, the skin may also be a target tissue for immunization against contact allergens as well as for administration of, for example, pre-immunization and booster doses of antigen as well as other therapeutically significant peptides. In addition, because IgE molecules are predominately present in mucosa and skin, use of these routes as points of entry according to the invention can be expected to be particularly effective in moderating allergic responses to antigen.

For use in primary immunizations against asthma-initiating antigens, intranasal administration means are most preferred. These means include inhalation of aerosol suspensions or insufflation of the polynucleotide compositions of the invention. Nebulizer devices suitable for delivery of polynucleotide compositions to the nasal mucosa are well-known in the art and will therefore not be described in detail here. To enhance absorption of the polynucleotide compositions of the invention, the compositions may include absorption promoters and/or detergents described in Section II-B, supra. To increase the population of APC's at the site of entry, a chemical irritant may also be employed.

In particular, the polynucleotides may include a chemical which irritates the outermost epithelial cells of the mucosa, thus provoking a sufficient immune response to attract additional APC's to the area. An example is a keratinolytic agent, such as the salicylic acid used in the commercially available topical depilatory cream sold by Noxema Corporation under the trademark NAIR™.

Dermal routes of administration, as well as subcutaneous injections, are useful in co-administration of other therapeutically significant peptides, as well as in immunizations and antigen boosters. The means of introduction for dermal routes of administration which are most preferred are those which are least invasive. Preferred among these means are transdermal transmission and epidermal administration.

For transdermal transmission, iontophoresis is a suitable method. Iontophoretic transmission may be accomplished using commercially available "patches" which deliver their product continuously through unbroken skin for periods of several days or more. Use of this method allows for controlled transmission of pharmaceutical compositions in relatively great concentrations, permits infusion of combination drugs and allows for contemporaneous use of an absorption promoter.

An exemplary patch product for use in this method is the LECTRO PATCH™ trademarked product of General Medical Company of Los Angeles, Calif. This product electronically maintains reservoir electrodes at neutral pH and can be adapted to provide dosages of differing concentrations, to dose continuously and/or to dose periodically. Preparation and use of the patch should be performed according to the manufacturer's printed instructions which accompany the LECTRO PATCH™ product; those instructions are incorporated herein by this reference.

Epidermal administration essentially involves mechanically or chemically irritating the outermost layer of the epidermis sufficiently to provoke an immune response to the irritant. Specifically, the irritation should be sufficient to attract APC's to the site of irritation. As discussed previously, it is believed that the APC's then take up and express the administered polynucleotide composition.

Alternatively, additional AIPCs can be attracted to the point of entry with mechanical irritant means. An exemplary mechanical irritant means employs a multiplicity of very narrow diameter, short tynes which can be used to irritate the skin and attract APC's to the site of irritation, to take up polynucleotide compositions transferred from the end of the tynes. For example, the MONO-VACC® old tuberculin test manufactured by Pasteur Merieux of Lyon, France contains a device suitable for introduction of polynucleotide compositions.

The device (which is distributed in the U.S. by Connaught Laboratories, Inc. of Swiftwater, Pa.) consists of a plastic container having a syringe plunger at one end and a tyne disk at the other. The tyne disk supports a multiplicity of narrow diameter tynes of a length which will just scratch the outermost layer of epidermal cells. Each of the tynes in the MONO-VACC®-kit is coated with old tuberculin; in the present invention, each needle is coated with a pharmaceutically effective polynucleotide composition or a mixture thereof. Use of the device is according to the manufacturer's written instructions included with the device product; these instructions regarding use and administration are incorporated herein by this reference to illustrate conventional use of the device. Similar devices which may also be used in this embodiment are those which are currently used to perform allergy tests.

D. Dosing Parameters for the Polynucleotide Compositions of the Invention

As noted above, it is probable that introduction of relatively low doses of asthma-initiating antigen-encoding polynucleotide to APC's using the method of the invention assists the asthma-initiating antigen in being expressed and retained intracellularly, thus limiting the extracellular availability of the asthma-initiating antigen for stimulation of IgE antibody production and formation of asthma-initiating antigen/IgE antibody complexes. Conversely, it appears that introduction of relatively "high" doses of asthma-initiating antigen-encoding polynucleotides (e.g., substantially greater than about 50 µg in mice) can stimulate production of IgE antibody at levels that are more comparable to those produced in mice injected subcutaneously with an asthma-initiating antigen, possibly due to extracellular release of antigen.

Thus, the preferred embodiment of the method for treatment of allergies of the invention will be one in which the asthma-initiating antigen-encoding polynucleotide is administered in "low" doses (e.g., preferably less than about 50 µg of polynucleotide in mice). Those of ordinary skill in the art will readily be able to determine an equivalent dosage level for use in humans. Those of ordinary skill in the art will be familiar with the course of dosing employed in asthma-initiating antigen immunotherapy (i.e., priming, booster and maintenance dosing), which course will be suitable for use in the method of the invention. Generally, it can be expected that murine equivalent doses of less than about 50 µg, and even less than about 10 µg, will be suitable for priming, booster and maintenance doses in humans.

Alternatively, the priming dose of asthma-initiating antigen-encoding polynucleotide may be followed by booster and/or maintenance doses of asthma-initiating antigen. Once an immunologic memory regarding the asthma-initiating antigen has been induced through introduction of an asthma-initiating antigen-encoding polynucleotide, that memory is maintained despite subsequent asthma-initiating antigen challenge.

Advantageously, because a polynucleotide that will operatively encode for an antigen is administered in lieu of the antigen itself, the quantity of foreign material being introduced to the host is relatively minimal. Moreover, routes of administration of polynucleotide compositions through skin or mucosa require a lower concentration of DNA to produce the same magnitude of immune response than does, for example, the intramuscular route of administration for the same compositions (e.g., about 10–50 fold lower; see, e.g., Example X). As a result, the invention lends itself well to the administration of polynucleotide compositions which code for up to several hundred different antigens for use in immunizing a host against more than one asthma-initiating antigen at a time. Thus, the invention also encompasses the administration of a peptide cocktail (i.e., mixture of polynucleotides) via expression of gene constructs containing, for example, up to 200 asthma-initiating antigen encoding polynucleotide sequences under the control of a single promoter.

Means to confirm the presence and quantity of expressed peptides are well-known to those skilled in the art and will not, therefore, be described in detail. Certain such means are illustrated in the Examples provided below; generally, they include immunoassays (such as enzyme-linked immunoabsorbent assays), PCR techniques, and immunohistological analyses performed according to techniques which are well known in the art. Dosages of the administered polynucleotides can be adjusted to achieve the desired level of expression based on information provided by these detection and quantification means as well as in vivo clinical signs known to practitioners skilled in the clinical arts.

Examples illustrating aspects of each embodiment of the invention are provided below. They should be regarded as illustrating rather than limiting the invention.

EXAMPLE I

Murine Model for the Airway Hyperreactivity of Allergic Asthma

Aeroasthma-initiating antigen challenged mice of different strains model the airway hyperreactivity seen in allergic asthma. Suitable murine strains for use in modeling the disease include Balb/c mice (which are IL-5+ and produce enhanced concentrations of IL-4 in response to CD4+ lymphocyte priming), C57BL/6 mice (which are IL-5 deficient, for detailed study of IL-5 induced tissue damage in asthma) and W/W$^V$ mice (which are mast cell deficient, for detailed study of mast cell activation in asthma).

Disease modeling mice are conveniently prepared by intraperitoneal or subcutaneous injection of ovalbumin ("OVA") in carrier (e.g., sterile saline), followed by antigen challenge with aerosolized antigen. For example, mice may be immunized with 25 μg OVA by subcutaneous injection (with or without adjuvant) weekly for 4–6 weeks, then challenged with 2 or 3 weekly aerosolizations of OVA at a concentration of 50 mg/ml in phosphate buffered saline (PBS) delivered in 20 minute intervals or at a concentration of 10 mg/ml 0.9% saline daily for about a week (in three 30 minute intervals daily). Nebulizer devices for use in the aerosolization are available from Aerotech II, CIS-US, Bedford, Mass.), with a nasal chamber adapted for murine nasal passages (e.g., a nose-only chamber from Intox Products, Albuquerque, N. Mex.). When driven by compressed air at a rate of 10 liters/min., the devices described produce aerosol particles having a median aerodynamic diameter of 1.4 μm.

Control mice are preferably littermates which are protein-antigen challenged without prior immunization. For further details concerning this animal model, those of skill in the art may wish to refer to Foster, et al., *J. Exp. Med.,* 195–201, 1995; and, Corry, et al., *J. Exp. Med.,* 109–117, 1996.

EXAMPLE II

Reduction of Eosinophil Accumulation in Lung Tissue in a Murine Asthma Model Three sets of 3–4 C57BL/6 mice, 6–10 weeks of age, were prepared as models of allergic asthma as described in Example I (subcutaneous injection of OVA followed by antigen challenge at a concentration of 50 mg OVA/ml PBS). Prior to immunization according to this scheme, two sets of the mice were pre-immunized with plasmid expression vectors which included genes for soluble OVA and ampicillin resistance (AmpR). One of the sets of pre-immunized mice received plasmids which encoded a chimeric antigen expressed as a product of fusion between the gene encoding OVA and the gene for the transferrin receptor. This "fusion" plasmid directs the production of a transmembrane, non-secreted protein at the site of immunization. Pre-immunization was performed by subcutaneous injection as described in Example VII.

On days 0, 7, 14 and 21, the two sets of pre-immunized mice and set of control mice were injected subcutaneously with 25 μg of OVA in 0.2 ml PBS. On days 26 and 31, each mouse was nebulized with 10 ml of 50 mg OVA/ml PBS using the nebulizer device described in Example I.

On day 32, each mouse was bled by tail snip (approximately 50 μl volume) into a 0.1 mM solution of PBS and EDTA. Red blood cells in solution were lysed with 150 mM NH$_4$Cl and 10 mM KHCO$_3$ in dH$_2$O then stained (Wright-Giesma stain). Lung lavage from each mouse was obtained after sacrifice by canalization of the trachea and lavage with 800 microliters PBS, then the lavage product was stained. Bone marrow samples from each mouse were obtained by flushing of extracted femur marrow with PBS. Histological specimens of lung and trachea tissue were obtained from the right lower lobe of the lung and trachea. Specimens were frozen, sectioned to a 5 micron width and stained with DAB peroxidase.

Eosinophil counts (with a single count=at least 300 cells) were obtained in each sample from each mouse. Results are expressed in the Table below as percent eosinophils compared to total leukocytes in each sample. In summary, the control mice (nos. 1–4) had an average of 41.3% eosinophils in the lung/trachea tissue samples. In contrast, the mice pre-immunized with the soluble OVA encoding plasmid (nos. 53–56 and 57–60) had 50% less eosinophil accumulation in these tissues compared to the control mice. Interestingly, the mice pre-immunized with the chimeric antigen encoding plasmid (nos. 65–68) had at least 90% reduction in eosinophil accumulation in these tissues as compared to the control mice. These data indicate that the IL-4 and IL-5 stimulated eosinophil accumulation in lung tissue which characterizes the late phase of allergic asthma is inhibited by polynucleotide immunization according the immunization scheme of the invention.

TABLE 1

| Mouse # | Bone Marrow | Peripheral blood | Broncheoalveolar Lavage |
|---|---|---|---|
| 1 | 9.3 | 2.0 | 47.4 |
| 2 | 6.0 >avg 10.3 | 4.4 >avg 5.0 | 65.0 >avg 43.1 |
| 3 | 14.3 | 12.1 | 24.2 |
| 4 | 11.4 | 1.4 | 35.7 |
| 53 | 0.3 | 3.6 | 45.0 |
| 54 | 4.2 >avg 3.9 | 5.8 >avg 4.2 | 20.4 >avg 25.4 |
| 55 | 0.8 | 2.5 | 10.9 |
| 56 | 10.2 | 4.8 | (trachea damaged) |
| 57 | 1.5 | 1.3 | 2.7 |
| 58 | 1.5 >avg 1.4 | 5.2 >avg 2.3 | 2.2 >avg 3.5 |
| 59 | 1.9 | 1.2 | 1.3 |
| 60 | 0.6 | 1.5 | 7.8 |
| 65 | 3.2 | 1.2 | 14.2 |
| 66 | 4.4 >avg 3.8 | 3.5 >avg 1.9 | 31.0 >avg 21.3 |
| 67 | 4.9 | 1.7 | 34.1 |
| 68 | 2.7 | 1.2 | 5.8 |

EXAMPLE III

Gene Expression Following Intranasal Introduction of a Polynucleotide Composition To test the level of protein expression following intranasal introduction of a polynucleotide composition (here, one to express influenza ribonucleoprotein from a plasmid under the control of a CMV promoter) was introduced to Balb/c mice in 3 groups of 6 intranasally. Levels of anti-NP IgG in peripheral blood before and after introduction of the plasmid at various serum dilutions were measured by ELISA as described in Example II. Blood was drawn from each mouse after intranasal introduction after 6 weeks.

Figure 2:
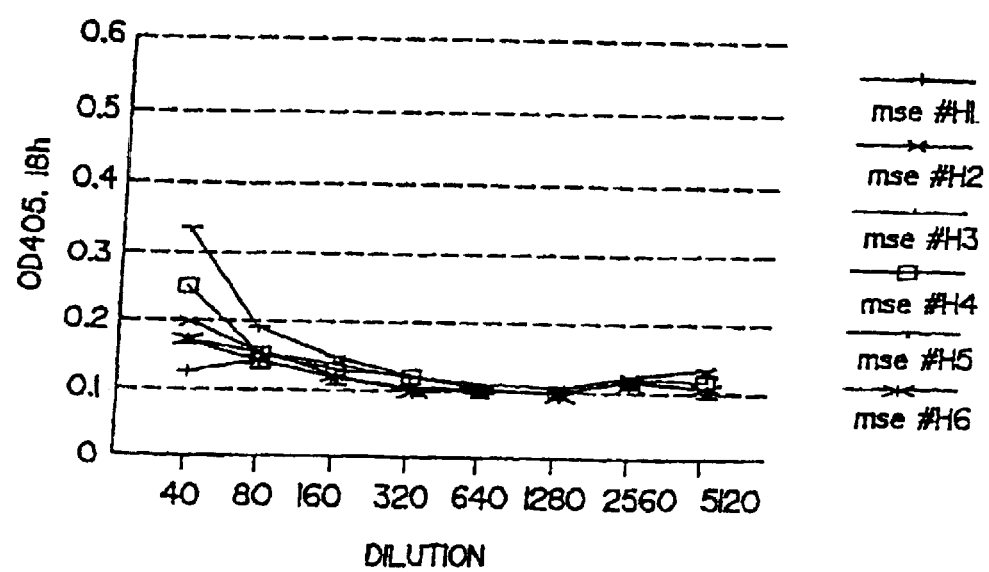
FIG. 2 depicts the results of an ELISA for anti-NP IgG in an unanesthetized group of Balb/c mice.
Figure 3:
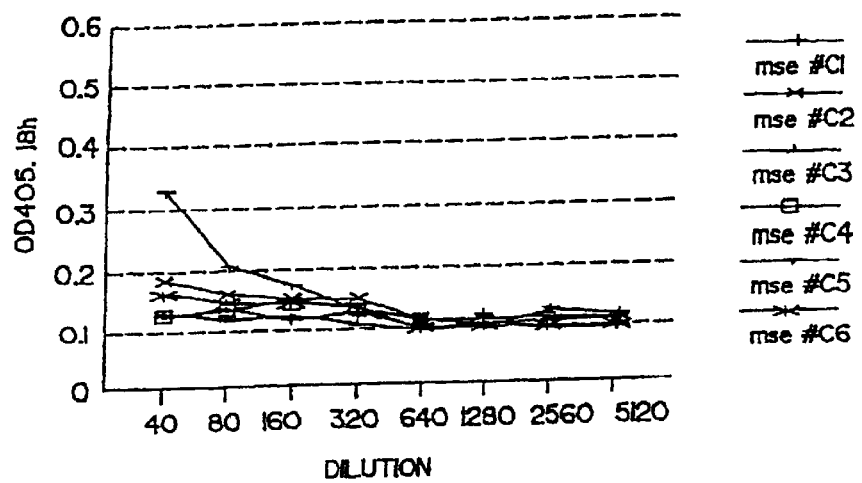
FIG. 3 depicts the results of an ELISA for anti-NP IgG in an anesthetized group of Balb/c mice.

FIGS. 1–3 graphically depict the results of the ELISA assays before and after intranasal introduction of the plasmid. The graphs plot ELISA titer against serum dilution. In FIG. 1, values are shown for individual mice from each group (#1–3) and an average value from all mice in each group (#G1–G3).

Without anesthesia, mice in a second group which received 3×7.5 μg of plasmid showed enhanced titers of antibody as compared to background (FIG. 1). These data are shown in FIG. 2.

A third group of mice received the same gravity of plasmid under anesthesia. Expression of RNP as indicated by titers of anti-NP IgG in these mice was substantially similar to the expression achieved in the unanesthetized mice. The data for the anesthetized mice are shown in FIG. 3.

Expression can be enhanced by additional use of absorption promoters, and prolonged by time-released promoters whose identity and use are known in the art such as those suggested in Chien, supra, at Ch. 5.

EXAMPLE IV

Histological Studies Showing Cell Uptake of Polynucleotide Compositions by Mononuclear Cells at the Point of Entry in Skin Three days after intradermal injection of the tails of naked pCMV-lacz (encoding β-galactosidase) into Balb/c mice, the mice were sacrificed. Tissue cultures were obtained at the point of entry for the plasmid and stained for *E. coli* β-galactosidase activity. A photograph (40×magnification) of a slide from the histological examination of-these cultures is contained in FIG. 4.

As shown in FIG. 4, uptake of the plasmid is shown (in blue) to be by mononuclear cells. The fibroblasts in the tissue samples are not stained, thus indicating that the plasmid was not taken up by these cells. The rounded, mononuclear cells which did take up the plasmid appear to be macrophages and/or other antigen presenting cells, which would indicate that uptake of the plasmid is by phagocytosis.

EXAMPLE V

Selective Induction of a Th1 Response after Administration of Polynucleotide Compositions According to the Invention In mice, IgG 2A antibodies are serological markers for a Th1 type immune response, whereas IgG 1 antibodies are indicative of a Th2 type immune response. Th2 responses include the allergy-associated IgE antibody class; soluble protein antigens tend to stimulate relatively strong Th2 responses. In contrast, Th1 responses are induced by antigen binding to macrophages and dendritic cells. Th1 responses are to be of particular importance in the treatment of allergies and AIDS.

To determine which response, if any, would be produced by mice who received polynucleotide compositions according to the invention, mice were vaccinated with PCMV Lac-Z or protein as described in the preceding example. At 2 week intervals, any IgG 2a and IgG 1 to β-galactosidase were measured by enzyme-linked immunoabsorbent assay (using antibodies specific for the IgG 1 and IgG 2A subclasses) on microtiter plates coated with the enzyme.

Figure 5:
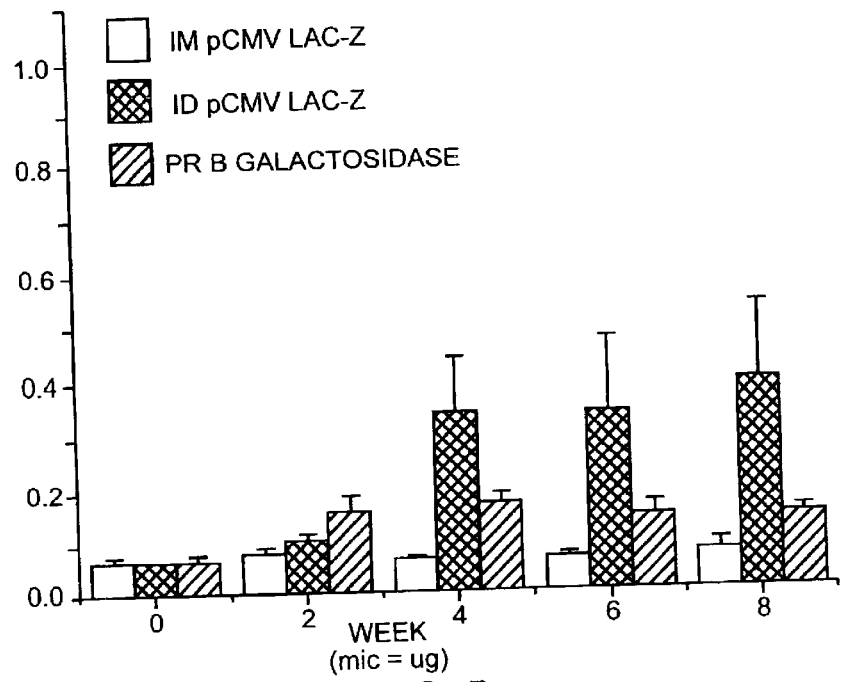
FIG. 5 depicts the results of an ELISA for IgG 2A type antibodies in sera for mice (1) injected intradermally or intramuscularly with a polynucleotide encoding β-galactosidase, or (2) the enzyme by intradermal injection.
Figure 6:
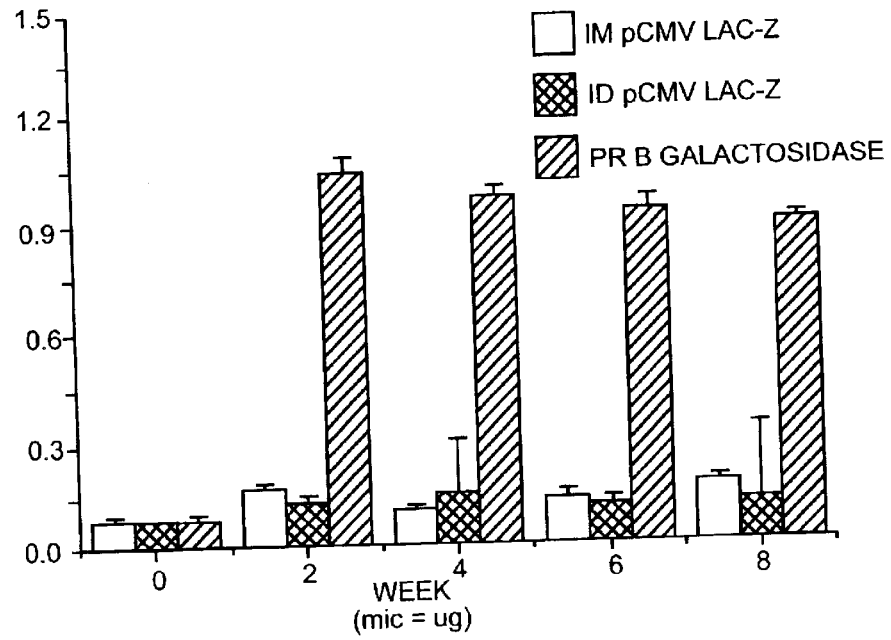
FIG. 6 depicts the results of an ELISA for IgG 1 type antibodies in sera for mice (1) injected intradermally or intramuscularly with a polynucleotide encoding β-galactosidase, or (2) the enzyme by intradermal injection.

As shown in FIG. 5, only the mice who received the plasmid by ID injection produced high titers of IgG 2A antibodies. As shown in FIG. 6, immunization of the mice with the enzyme itself ("PR") induced production of relatively high titers of IgG 1 antibodies. In the IM injected mice, low titers of both IgG 2A and IgG 1 antibodies were produced without apparent selectivity. The data shown in the FIGURES comprise averages of the values obtained from each group of 4 mice.

Figure 7:
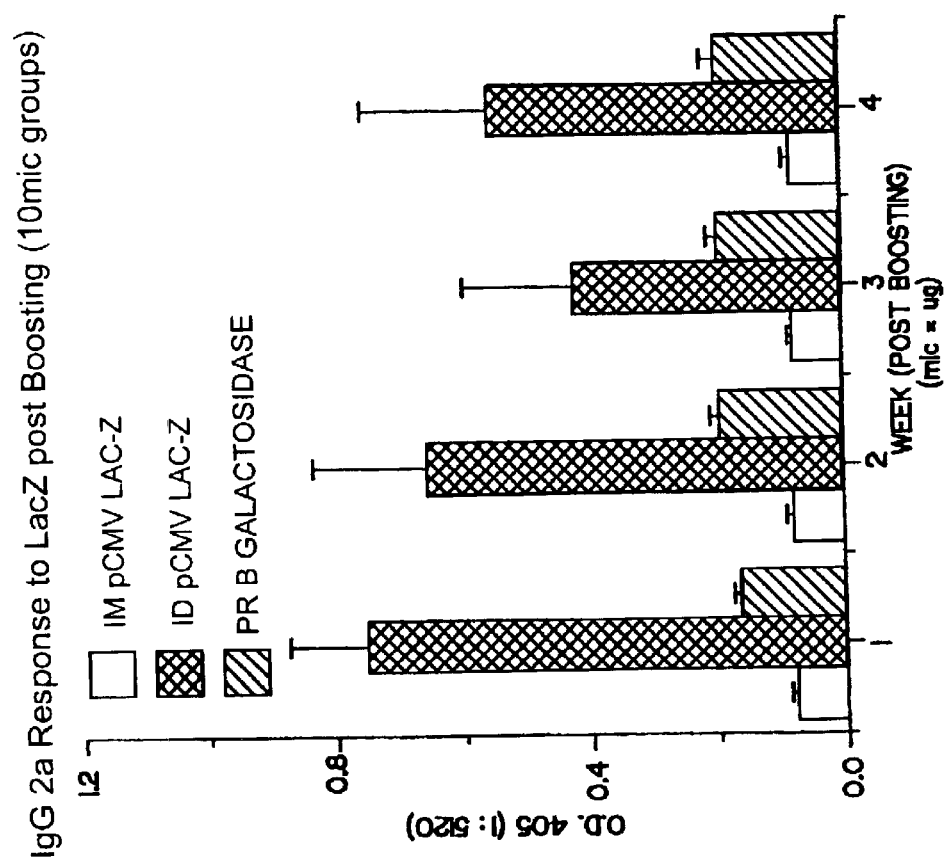
FIG. 7 depicts the results of an ELISA for IgG 2A type antibodies in sera of the mice described with respect to FIG. 5 after a booster injection of antigen.
Figure 8:
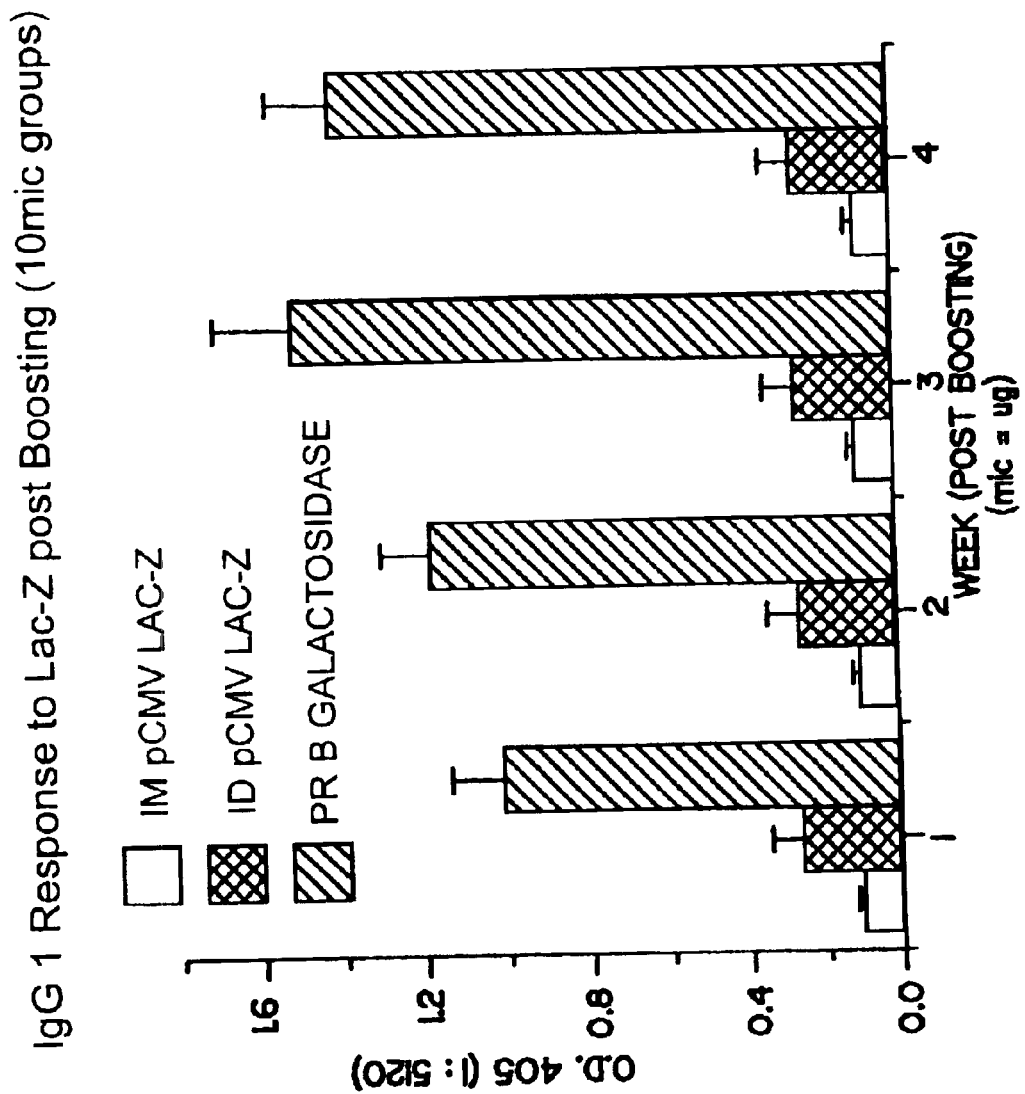
FIG. 8 depicts the results of an ELISA for IgG 1 type antibodies in sera of the mice described with respect to FIG. 6 after a booster injection of antigen.

To determine the stability of the antibody response over time, the same group of animals were boosted with 0.5 μg of enzyme injected intradermally. As shown in FIGS. 7 and 8 boosting of ID injection primed animals with the enzyme induced a nearly 10-fold rise in IgG 2A antibody responses (i.e., the antibody titer rose from 1:640 to 1:5120), but did not stimulate an IgG 1 response. These data indicate that the selective Th1 response induced by ID administration of polynucleotide compositions is maintained in the host, despite subsequent exposure to antigen.

EXAMPLE VI

Th1 Responses in Mice after Administration of Polynucleotide Compositions with a Mechanical Irritant The experiments described in Example V were repeated in separate groups of mice, except that (1) only a priming dose was tested, and (2) the pCMV Lac-Z plasmid was administered to one group of 4 mice using the MONO-VACC® tyne device described in the disclosure, while β-galactosidase protein (10 μg) was administered to another group of 4 mice by intradermal (ID) injection.

Figure 9:
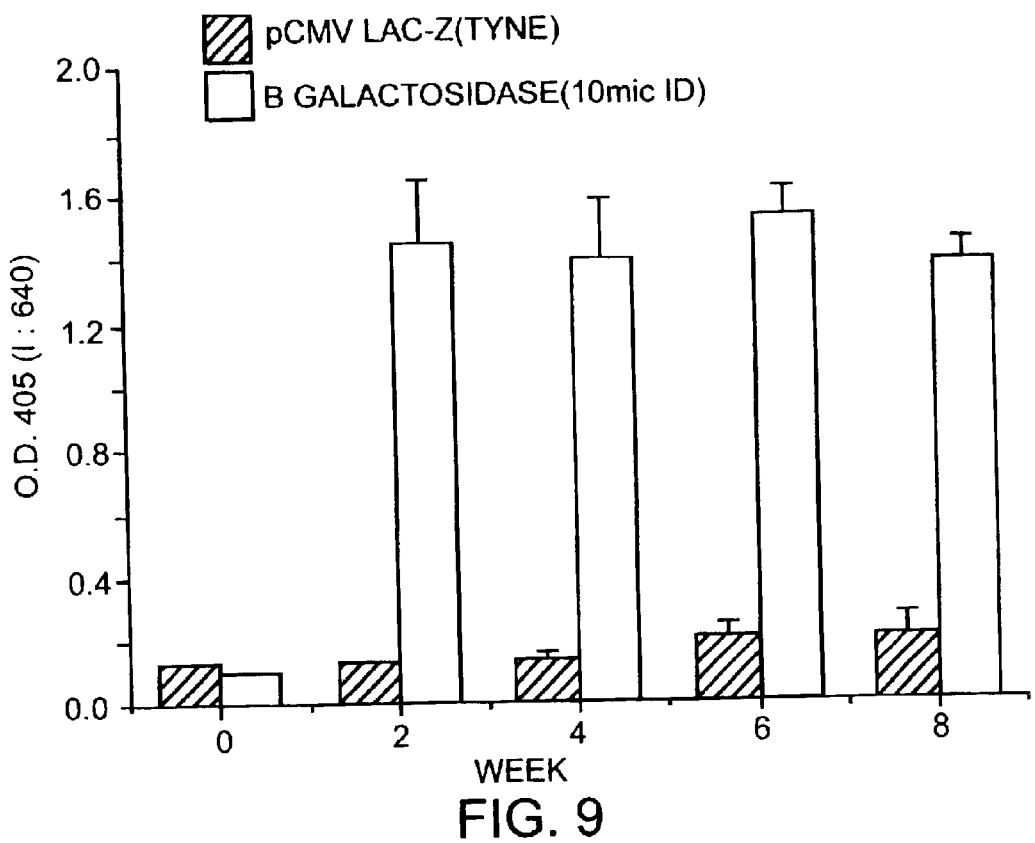
FIG. 9 depicts the results of an ELISA for IgG 2A type antibodies in sera for mice (1) introduced by scratching the skin with tynes coated with a polynucleotide encoding β-galactosidase, or (2) the enzyme by intradermal injection.
Figure 10:
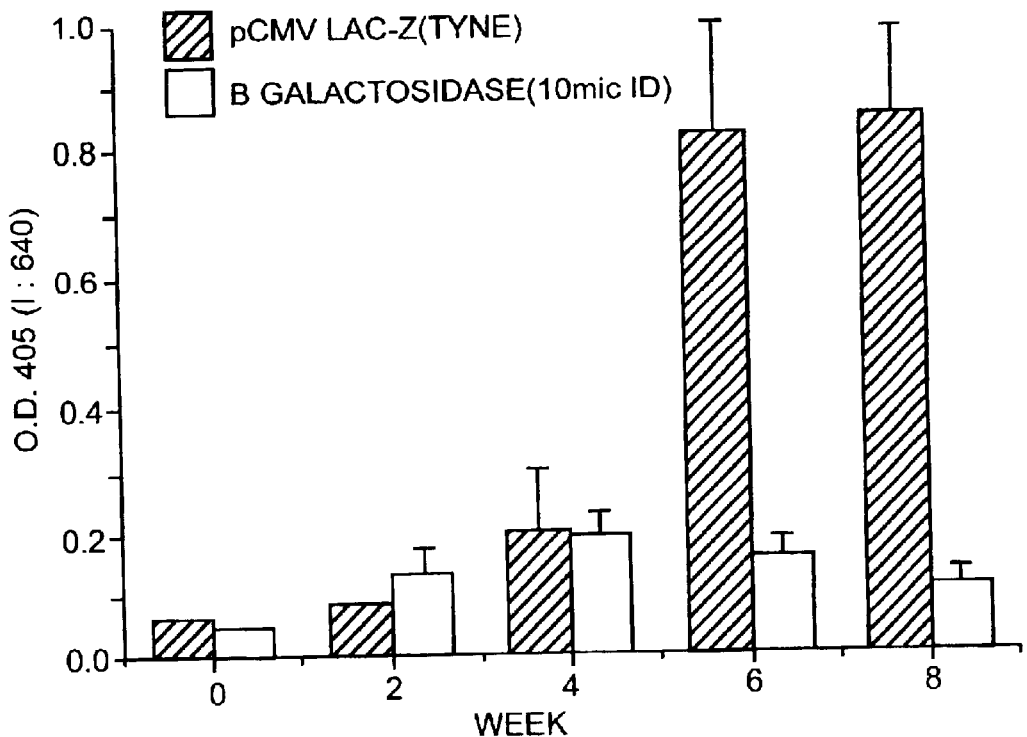
FIG. 10 depicts the results of an ELISA for IgG 1 type antibodies in sera for mice (1) introduced by scratching the skin with tynes coated with a polynucleotide encoding β-galactosidase, or (2) the enzyme by intradermal injection.

As shown in FIG. 9, the mice who received plasmid produced relatively low titers of IgG 1 antibody compared to the mice who received the protein. In contrast, as shown in FIG. 10, the mice who received plasmid produced substantially higher titers of IgG 2A antibody as compared to the mice who received the protein.

Interestingly, the mice who received the plasmid via scratching of their skin with the tyne device produced even higher titers of IgG 2A antibody than did the mice who received the same plasmid via ID injection (both of which groups produced higher titers of IgG 2A antibody than did the mice who received the plasmid via IM injection). These results indicate that scratching of skin with the tyne device attracts greater number of APC's to the "injured" point of entry for the polynucleotide compositions and are consistent with the theory that APC's are more efficient targets for gene administration and expression than are muscle or other somatic cells. The data shown in the FIGURES comprise averages of the values obtained from each group of 4 mice.

EXAMPLE VII

Suppression of IgE Antibody Response to Antigen by Immunization with Antigen-Encoding Polynucleotides Five to eight week old Balb/c mice were immunized with one of two recombinant expression vectors: pCMV-Lac-Z or a control plasmid, pCMV-BL (which does not encode for any insert peptide). A third group of the mice received injections of antigen (β galactosidase). Plasmid DNA was purified and its endotoxin content reduced to 0.5–5 ng/1mg DNA by extraction with TRITON X-114 (Sigma, St. Louis, Mo.). Before inoculation, pDNA was precipitated in ethanol, washed with 70% ethanol and dissolved in pyrogen free normal saline.

Immunization was by intradermal injection of plasmid DNA loaded onto separate tynes of a MONO-VACC® multiple tyne device (Connaught Lab, Inc., Swiftwater, Pa.). Briefly, the tyne devices were prepared after extensive washing in DDW and overnight soaking in 0.5% SDS (sulfated dodecyl saline), washed again in DDW, soaked overnight in 0.1N NaOH, washed again in DDW and dried at 37° C. for 8 hours. Six μl of plasmid DNA dissolved in normal saline were pipetted onto the tynes of the tyne device just prior to each inoculation described below. The total amount of pDNA loaded on the device per inoculation was 25 μg each of pCMV-Lac-Z and pCMV-BL. For purposes of estimating actual doses, it was assumed that less than 10% of the pDNA solution loaded onto the tyne device was actually introduced on injection of the tynes into intradermal tissue. Each mouse was treated 3 times with 2 inoculations of each plasmid in a one week interval injected intradermally at the base of the tail. Another group of mice received a single intradermal injection in the base of the tail of 10 μg of β galactosidase protein (dissolved in 50 μl of normal saline) in lieu of pDNA.

Toward inducing an IgE antibody response to subsequent asthma-initiating antigen challenge, each group of mice was injected once intraperitoneally with 0.1 ml of phosphate buffered saline (PBS) solution containing 1 μg of antigen (β galactosidase; Calbiochem, San Diego, Calif.) and 3 mg of ALUM aluminum hydroxide as adjuvant (Pierce Chemical, Rockford, Ill.) 14 weeks after the initial immunization. Total IgE was assayed in sera from the mice 4 times over the subsequent 4 consecutive weeks.

IgE was detected using a solid phase radioimmunoassay (RAST) in a 96 well polyvinyl plate (a radioisotopic modification of the ELISA procedure described in Coligan, "*Current Protocols In Immunology*" Unit 7.12.4, Vol. 1, Wiley & Sons, 1994), except that purified polyclonal goat antibodies specific for mouse ε chains were used in lieu of antibodies specific for human Fab. To detect anti-Lac-Z IgE, the plates were coated with β galactosidase (10 μg/ml). The lowest IgE concentration measurable by the assay employed was 0.4 ng of IgE/ml.

Figure 13:
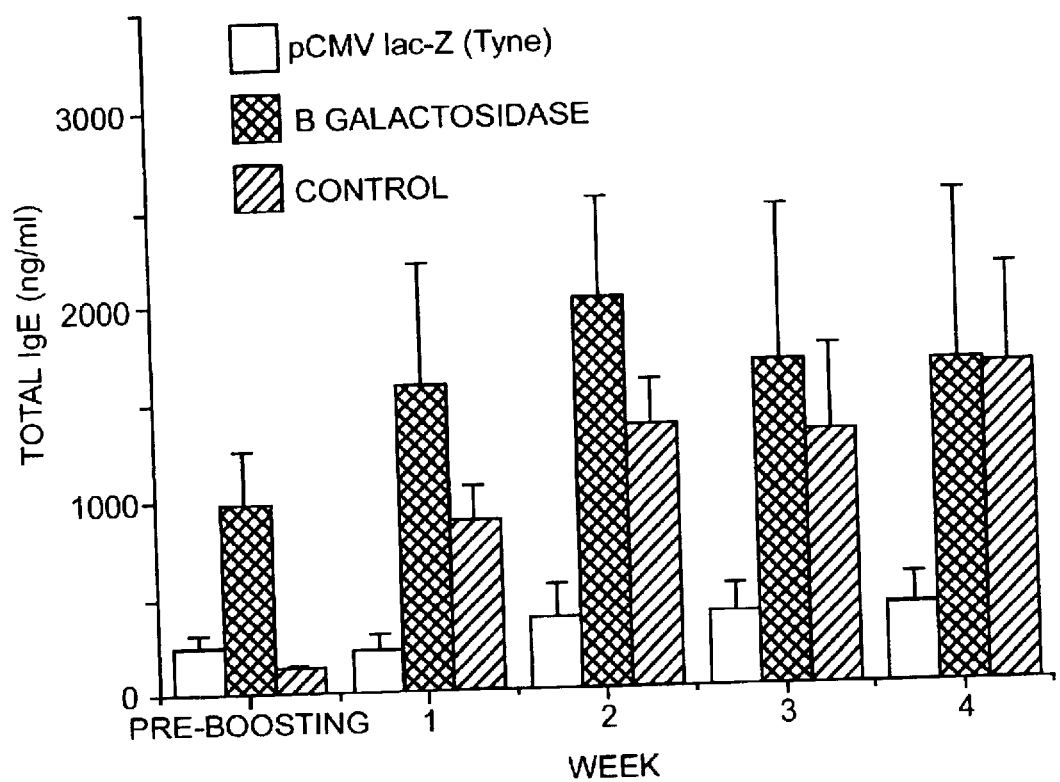
FIG. 13 depicts the results of an ELISA for total IgE antibody levels in mice after immunization with an antigen-encoding plasmid (pCMV-Lac-Z), the antigen itself (β galactosidase), or a control (non-encoding) plasmid (pCMV-BL).

As shown in FIG. 13, mice injected with pCMV-Lac-Z produced only low levels of total IgE antibody (averaging about 250 CPM in RAST) as compared to mice injected with β galactosidase (averaging about 1000 CPM in RAST). Moreover, IgE levels in the plasmid injected mice remained consistently low (averaging about 250–450 CPM) despite boosting with protein (indicating that tolerance was acquired in these mice on initial immunization), while IgE levels in the protein injected mice rose substantially (averaging about 1500 to 2000 CPM) after boosting, then eventually tapered off to control levels at week 4 as tolerance was acquired by the protein injected mice through repeated exposure to the protein antigen.

Figure 14:
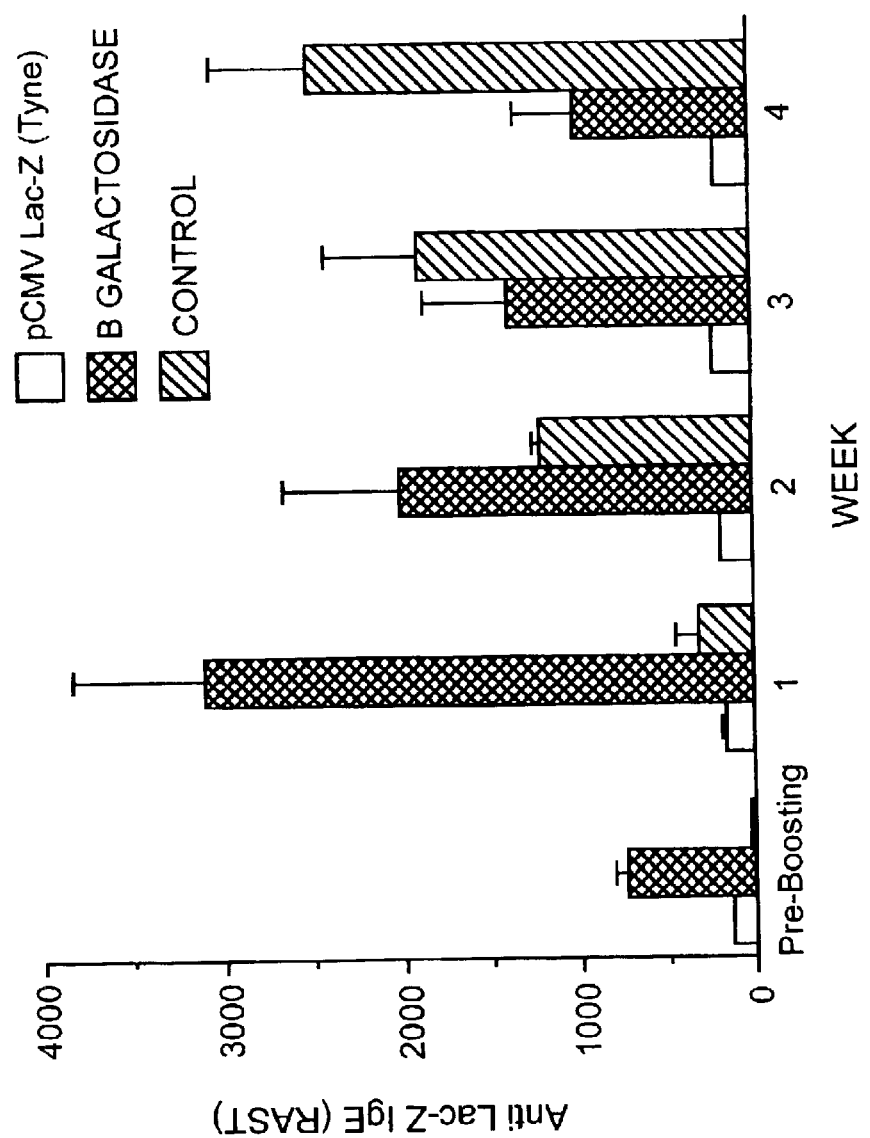
FIG. 14 depicts the results of an ELISA for antigen-specific IgE antibody levels in mice after immunization with an antigen-encoding plasmid (pCMV-Lac-Z), the antigen itself (β galactosidase), or a control (non-encoding) plasmid (pCMV-BL).

Measuring specifically the anti-antigen response by each group of mice, as shown in FIG. 14, anti-Lac-Z IgE levels in the plasmid injected mice again were consistently low both before and after boosting (averaging about 250 CPM in RAST), while the protein injected mice developed high levels of anti-Lac-Z, particularly after the first antigen booster injection, when anti-Lac-Z levels in the mice rose to an average of about 3000 CPM. Consistent with acquisition of tolerance, anti-Lac-Z IgE levels in the protein injected mice declined over time, but continued to rise in the control mice who had not received any immunization to β galactosidase.

These data show that the plasmid injected mice developed an antigen specific Th1 response to the plasmid expression product with concomitant suppression of IgE production, while tolerance was acquired in the protein injected mice only after development of substantially higher levels of total and antigen specific IgE antibodies.

EXAMPLE VIII

IL-4 and INFγ Levels in Mice after Immunization with Antigen or Antigen-Encoding Polynucleotides To confirm that the results shown by the data presented in Examples V through VII can be attributed to the selective induction of Th1 responses (e.g., INFγ secretion) in plasmid injected mice (which responses are believed to exert a negative effect on IgE stimulatory Th2 responses; e.g., secretion of IL-2), levels of IL-2 and INFγ were assayed in the sera of the plasmid and protein injected mice of Example VII at week one, after one booster injection of antigen. IL-2 levels were assayed using a commercial kit; INFγ levels were assayed with an anti-INFγ murine antibody assay (see, e.g., Coligan, "*Current Protocols in Immunology*", Unit 6.9.5., Vol. 1, Wiley & Sons, 1994).

Figure 15:
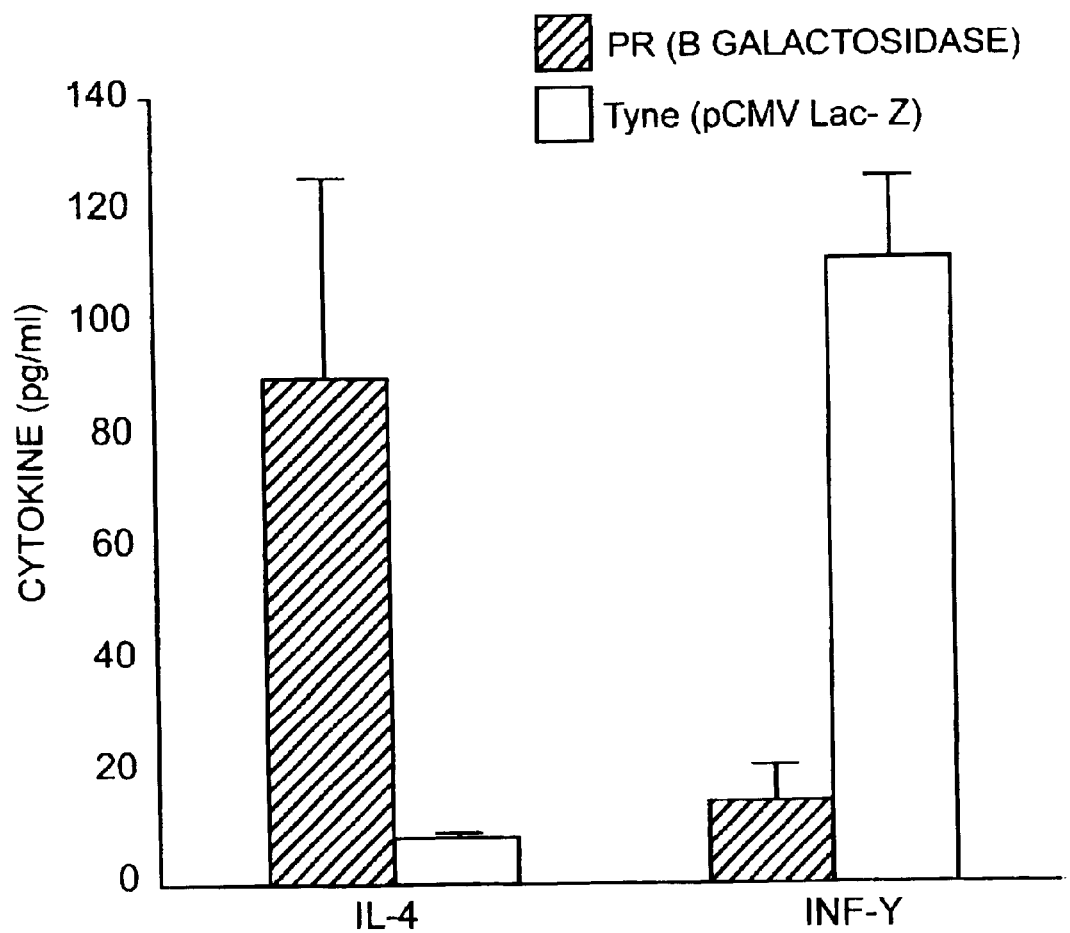
FIG. 15 depicts the results of an ELISA for levels of IL-2 and INFγ after immunization of mice with an antigen-encoding plasmid (pCMV-Lac-Z) or the antigen itself (β galactosidase).

As shown in FIG. 15, levels of IgE stimulatory IL-4 in the protein injected mice were substantially higher than in plasmid injected mice (by about a 9:1 ratio). Conversely, levels of INFγ in the plasmid injected mice were substantially higher than in the protein injected mice (by a ratio of about 11:1).

EXAMPLE IX

Production and Maintenance of Cytotoxic T Lymphocytes after Immunization with Antigen or Antigen-Encoding Polynucleotides As discussed elsewhere above, it is believed that cytotoxic T lymphocytes (CTLs) suppress Th2 cell activity, which in turn would suppress the ability of such cells to stimulate the development of IgE antibodies. To confirm whether the plasmid injected mice developed CTL's and maintained the anti-antigen protection afforded thereby, CTL levels in plasmid injected and control mice were measured.

The plasmid injected mice were immunized with a plasmid encoding influenza ribonucleoprotein. Control mice received a plasmid that did not code for an insert peptide (pCMV-BL). The total amount of pDNA loaded on the tyne device per inoculation was 50 μg of pCMV-NP and 25 μg of pCMV-BL.

36 weeks after immunization, the mice were sacrificed and splenocytes were removed for use in standard nixed lymphocyte cultures. The cultures were grown in the presence of a known synthetic peptide representing the major $H-2^d$ restricted CTL epitope of the NP protein. The cultures were assayed for anti-NP CTL activity 5–6 days later using NP peptide pulsed syngeneic P815 tumor cells (ATCC # TIB64, American Type Culture Collection, 10801 University Boulevard, Manassas, Va. 20110-2209) as targets.

Figure 16:
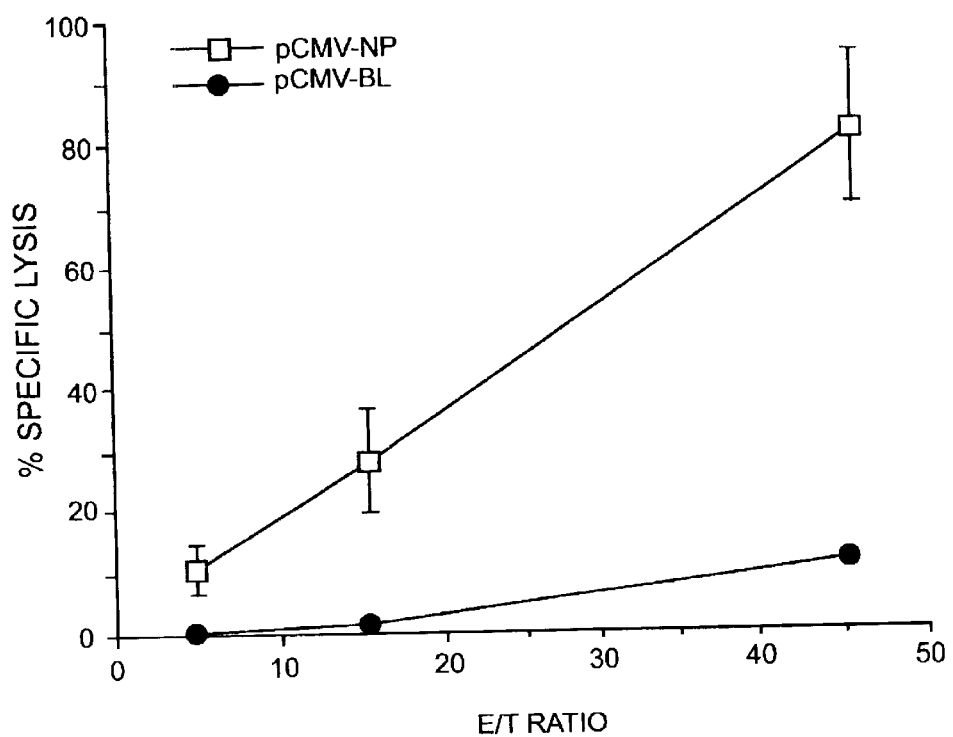
FIG. 16 depicts the results of an assay to detect antigen-specific cell lysis by T lymphocytes from mice immunized by epidermal administration of pCMV-NP plasmid.
Figure 17:
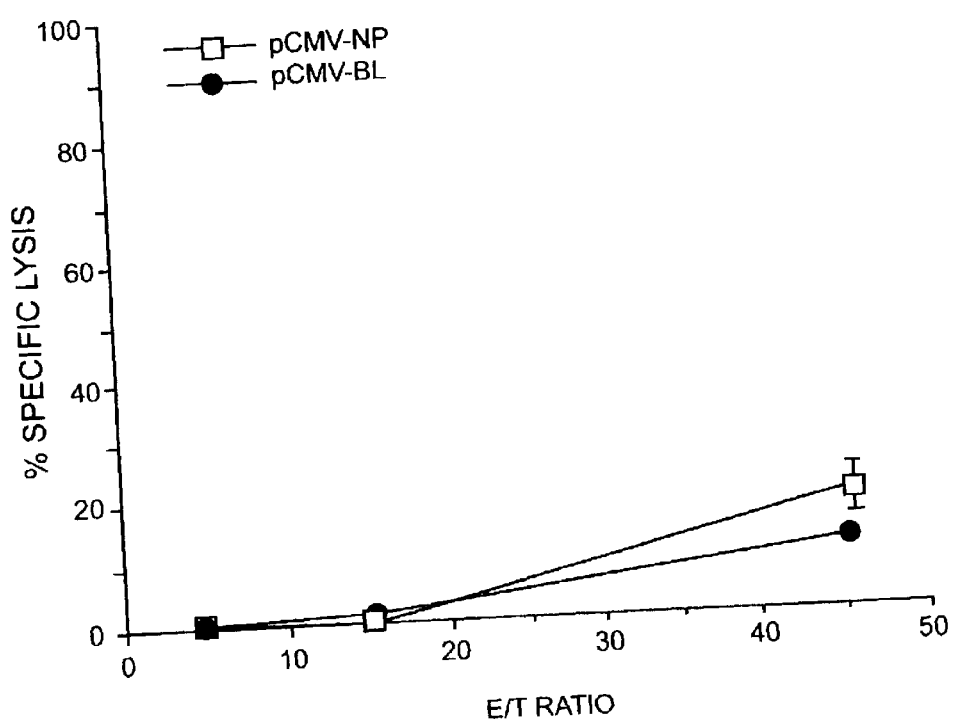
FIG. 17 depicts the results of an assay to detect antigen-specific cell lysis by T lymphocytes from the mice described in FIG. 16 in absence of pulsing of the cells with the antigen.

As shown in FIG. 16, mixed lymphocyte cultures prepared from the pCMV-NP injected animals displayed high levels of specific anti-NP cytolytic activity, reaching 10%, 30% and 80% of specific lysis at an effector to target (E/T) ratio of 5:1, 15:1 and 45:1, respectively. Control mice only displayed 1%, 1% and 9% under the same conditions. Further, in absence of exposure to the $H-2^d$ epitope peptide, there were not significant differences in CTL activity in the pCMV-NP injected and control mice (FIG. 17). These data indicate selective activation of Th1 cells in the pCMV-NP injected mice.

EXAMPLE X

Prolonged Immunologic Memory Induced by Antigen Stimulation of T Cells after Administration of Polynucleotide Compositions 0.1, 1, 10 and 100 μg of polynucleotide compositions in plasmid form (0.5–5 ng/1 mg DNA endotoxin content) encoding the *E. coli* enzyme β-galactosidase under the control of the CMV promoter ("pCMV Lac-Z") were administered to groups of 4 mice\dosage\route either intramuscularly ("IM") or intradermally ("ID"). For comparison, another group of 4 mice\dosage received 100 μg β-galactosidase protein ("PR") Intradermally. All injections were made using 50 μl normal saline as carrier. IM and ID injections were made with a 0.5 ml syringe and a 28.5 gauge needle. Antibodies were thereafter measured by enzyme-linked immunoabsorbent assay at 2 week intervals.

Briefly, total antibodies were measured using β-galactosidase (Calbiochem, CA) as the solid phase antigen. Microtiter plates (Costar, Cambridge, Mass.) were coated with 5 μg of antigen dissolved in 90 mM borate (pH 8.3) and 89 mM NaCl (i.e., borate buffered saline; BBS) overnight at room temperature and blocked overnight with 10 mg/ml of bovine serum albumin in BBS.

Serum samples were serially diluted in BBS starting at a 1:40 dilution for the first 8 weeks, them a 1:320 dilution thereafter. These samples were added to the plates and stored overnight at room temperature. Plates were washed in BBS+ 0.05% polysorbate 20, then reacted with a 1:2000 dilution of alkaline phosphatase labeled goat anti-mouse IgG antibody (Jackson Immunoresearch Labs., West Grove, Pa.) for 1 hour at room temperature, or were reacted with a 1:2000 dilution of alkaline phosphatase labeled goat anti-mouse IgG 1 antibody (Southern Biotech of AL), or were reacted with a 1:500 dilution of alkaline phosphatase labeled rat anti-mouse IgG 2A antibody (Pharmingen, of CA), under the same conditions. Plates were washed again, then a solution of 1 mg/ml of p-nitrophenol phosphate (Boehringer-Mannheim, Indianapolis, Ind.) in 0.05 M carbonate buffer (pH 9.8), containing 1 mM $NgCl_2$ was added. Absorbance at 405 nm was read 1 hour after addition of substrate to the plates.

Figure 18:
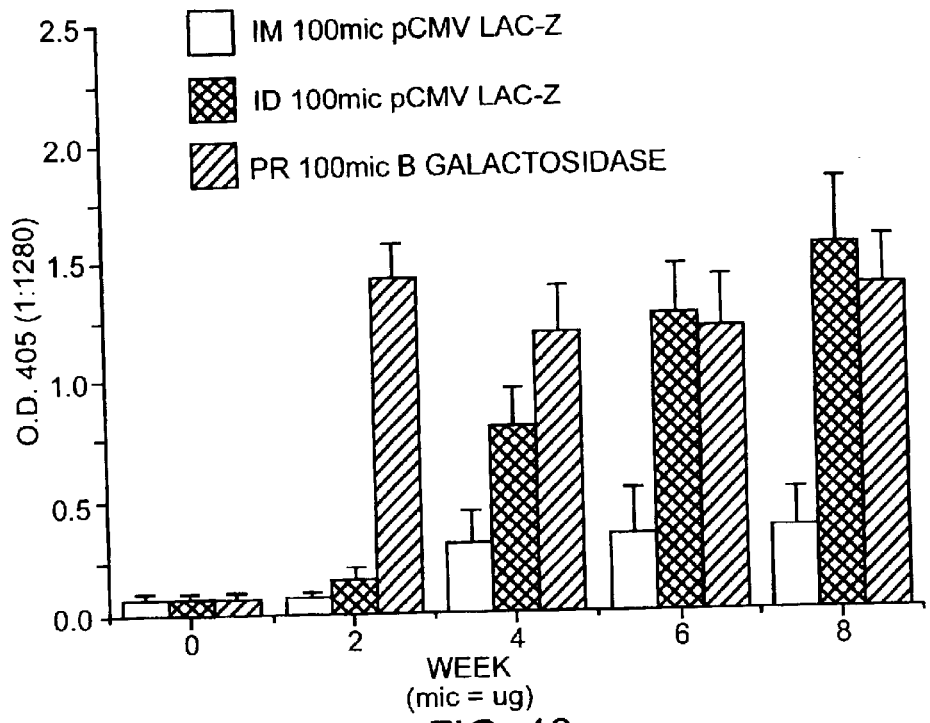
FIG. 18 depicts the results of an ELISA for anti-β-galactosidase antibodies after administration of (1) a polynucleotide encoding the enzyme by intramuscular or intradermal injection, and (2) the enzyme by intradermal injection.

As shown in FIG. 18, antibody responses of equivalent magnitude were induced in the animals who had received the pCMV Lac-Z plasmids by ID injection and the animals who had received the PR, while lesser antibody responses were measured in the animals who had received the pCNV Lac-Z plasmids by IM injection.

To assess for T cell memory, the animals were then boosted with 0.5 μg of PR at a separate site by ID injection. If these animals had developed memory T cells to control production of antibody to β-galactosidase, they would be expected to mount a more vigorous immune response after boosting with soluble protein antigen than had been demonstrated in response to the priming dose of antigen.

Figure 19:
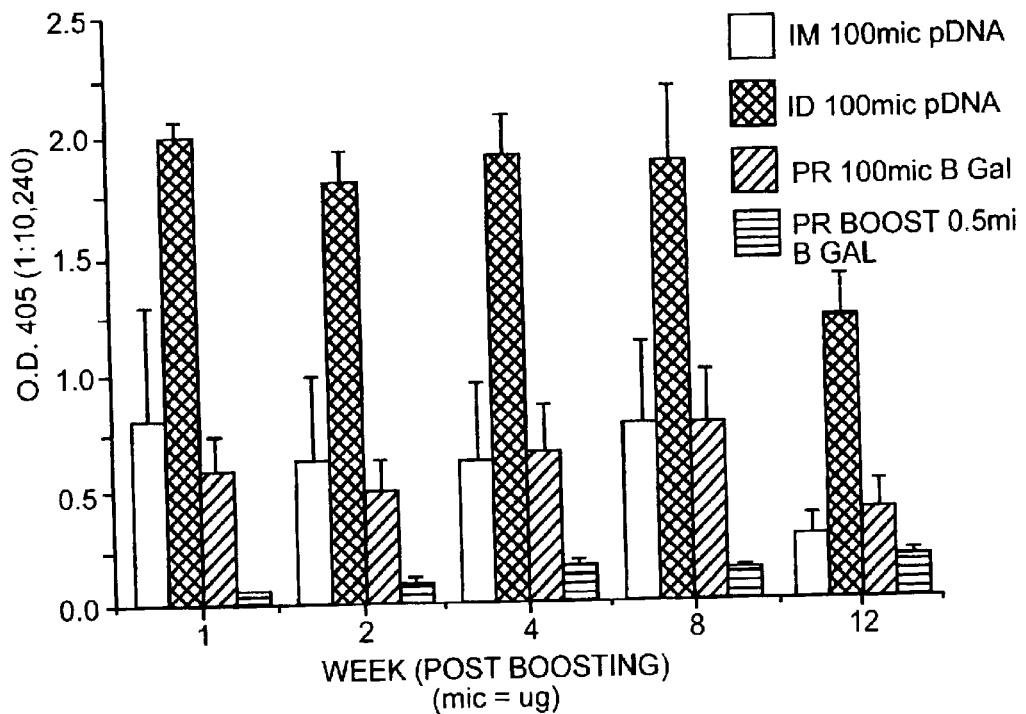
FIG. 19 depicts the results of an ELISA for anti-β-galactosidase antibodies in sera from the mice described with respect to FIG. 18 after a booster injection of antigen.

As shown in FIG. 19, it is clear that the animals which had received ID injections of pCMV Lac-Z plasmid had developed substantially better immunological memory than did animals which had received either IM injections of plasmid or of PR. Further, the memory which was developed by the ID injected animals persisted for a minimum of about 12 weeks.

The invention claimed is:

1. A method for treating both the early and late phases of allergic asthma in a host, the method comprising:

introducing a naked polynucleotide composition into the host's mucosa or skin, wherein the naked polynucleotide comprises a recombinant expression vector which encodes an asthma-initiating antigen;

wherein the asthma-initiating antigen is expressed in an antigen presenting cell, and wherein Th1 lymphocytes are stimulated in preference to Th2 lymphocytes.

2. The method according to claim 1 wherein the polynucleotide composition is administered in an amount sufficient to suppress antigen-stimulated IgE antibody production.

3. The method according to claim 1 wherein the polynucleotide composition is introduced into the respiratory passages of the host.

4. The method according to claim 3 wherein the naked polynucleotide composition is aerosolized.

5. The method according to claim 1 wherein the naked polynucleotide composition is introduced into the skin of the host.

6. The method of claim 1, wherein eosinophil infiltration of lung tissue in the host is suppressed.

* * * * *